United States Patent
Martin

(10) Patent No.: US 7,812,133 B2
(45) Date of Patent: Oct. 12, 2010

(54) ANTI-OX40L ANTIBODIES AND METHODS USING SAME

(75) Inventor: Flavius Martin, Hayward, CA (US)

(73) Assignee: Genentech, Inc, South San Francisco, CA (US)

(*) Notice: Subject to any disclaimer, the term of this patent is extended or adjusted under 35 U.S.C. 154(b) by 0 days.

(21) Appl. No.: 12/097,733

(22) PCT Filed: Dec. 15, 2006

(86) PCT No.: PCT/US2006/062173
§ 371 (c)(1),
(2), (4) Date: Oct. 7, 2008

(87) PCT Pub. No.: WO2007/133290
PCT Pub. Date: Nov. 22, 2007

(65) Prior Publication Data
US 2009/0053230 A1  Feb. 26, 2009

Related U.S. Application Data

(60) Provisional application No. 60/751,377, filed on Dec. 16, 2005.

(51) Int. Cl.
| | |
|---|---|
| *C07K 16/00* | (2006.01) |
| *C12P 21/08* | (2006.01) |
| *A61K 39/395* | (2006.01) |
| *A61K 39/00* | (2006.01) |
| *C07H 21/04* | (2006.01) |
| *C12N 15/00* | (2006.01) |
| *C12N 15/64* | (2006.01) |
| *C12P 21/04* | (2006.01) |

(52) U.S. Cl. ............... 530/387.1; 530/387.3; 530/388.1; 530/388.85; 424/130.1; 424/133.1; 424/141.1; 424/152.1; 536/23.53; 435/320.1; 435/91.4; 435/69.6

(58) Field of Classification Search .................. None
See application file for complete search history.

(56) References Cited

U.S. PATENT DOCUMENTS

| | | | |
|---|---|---|---|
| 5,457,035 | A | 10/1995 | Baum et al. |
| 6,333,035 | B1 | 12/2001 | Sugamura et al. |
| 6,528,623 | B2 | 3/2003 | Godfrey et al. |
| 7,291,331 | B1 | 11/2007 | Croft et al. |
| 7,501,496 | B1 * | 3/2009 | Endl et al. ............... 530/387.3 |
| 2004/0009174 | A1 | 1/2004 | Arndt et al. |
| 2005/0034179 | A1 | 2/2005 | Sugamura et al. |
| 2005/0042718 | A1 | 2/2005 | Bazin et al. |
| 2005/0069548 | A1 | 3/2005 | Hussell et al. |
| 2006/0002929 | A1 | 1/2006 | Khare et al. |
| 2006/0069548 | A1 | 3/2006 | Matsuura |

FOREIGN PATENT DOCUMENTS

| | | |
|---|---|---|
| WO | 95/12673 | 5/1995 |
| WO | 95/21915 | 8/1995 |
| WO | 99/15200 | 4/1999 |
| WO | 03/059245 | 7/2003 |
| WO | 03/082919 | 10/2003 |
| WO | 2004/019866 | 3/2004 |
| WO | 2006/029879 A2 | 3/2006 |
| WO | 2008/106116 A2 | 9/2008 |

OTHER PUBLICATIONS

Rudikoff, Giusti, Cook, and Sharff. Single amino acid substitution altering antigen-binding specificity. Proceedings of the National Academy of Sciences, 1982. vol. 79, pp. 1979-1983.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Chen, Wiesmann, Fuh, Li, Christinger, Mc Kay, De Vos, and Lowman. Selection and analysis of an optimized anti-VEGF antibody: crystal structure of an affinity-matured Fab in complex with antigen. Journal of Molecular Biology, 1999. vol. 293, pp. 865-881.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Wu, Nie, Huse, and Watkins. Humanization of a murine monoclonal antibody by simultaneous optimization of framework and CDR residues. Journal of Molecular Biology, 1999. vol. 294, pp. 151-162.*
Granziero, Krajewski, Farness, Yuan, Courtney, Jackson, Peterson, and Vitiello. Adoptive immunotherapy prevents prostate cancer in a transgenic animal model. European Journal of Immunology, 1999. vol. 29, pp. 1127-1138.*
Byers. What can randomized controlled trials tell us about nutrition and cancer prevention? CA Cancer Journal, 1999. vol. 49, pp. 353-361.*
Akiba, et al., "CD28-Independent Costimulation of T Cells by OX40 Ligand and CD70 on Activated B Cells" *The Journal of Immunology* pp. 7058-7066 (1999).
Miura et al., "Molecular cloning and characterization of a novel glycoprotein, gp34, that is specifically induced by the human T-cell leukemia virus type I transactivator p40tax" *Molecular & Cellular Biology* 11(3) :1313-1325 (1991).

(Continued)

*Primary Examiner*—Anne M. Gussow
(74) *Attorney, Agent, or Firm*—Cara Coburn

(57) ABSTRACT

The invention provides anti-OX40L antibodies, and compositions comprising and methods of using these antibodies.

37 Claims, 8 Drawing Sheets

OTHER PUBLICATIONS

Nohara, C., et al., "Amelioration of Experimental Autoimmune Encephalomyelitis with Anti-OX40 Ligand Monoclonal Antibody: A Critical Role for OX40 Ligand in Migration, but not Development, of Pathogenic T Cells" *Journal of Immunology* 41:2108-2115 (2001).

Satake, Y., et al., "Characterization of Rat OX40 Ligand by Monoclonal Antibody" *Biochemical and Biophysical Research Communications* 270:1041-1048 (2000).

Totsuka, et al., "Therapeutic Effect of Anti-OX40L and Anti-TNF-α MAbs in a Murine Model of Chronic Colitis" *Am. J. Physio. Gastrointest Liver Physiol* 284:G595-G603 (2003).

Tozawa et al., "Species-dependent antigenicity of the 34-kDa glycoprotein found on the membrane of various primate lymphocytes transformed by human T-cell leukemia virus type-I (HTLV-I) and simian T-cell leukemia virus (STLV-I)" *Int. J. Cancer* 41:231-238 (1988).

Baum et al., "Molecular characterization of murine and human OX40/OX40 ligand systems: identification of a human OX40 ligand as the HTLV-1-regulated protein gp34" *EMBO Journal* 13 (17) :3992-4001 (1994).

Burgess et al., "Detection and characterization of OX40 ligand expression in human airway smooth muscle cells: a possible role in asthma?" *J Allergy Clin Immunol.* 113 (4) :683-9 (Apr. 2004).

Godfrey, W. et al., "Stan-40, a new member of the FAS-TNFr superfamily expressed selectively on activated, human CD4+ T cells" *J. Cellular Biochemistry* (V370)Suppl. 18D:355 (1994).

Higgins et al., "Regulation of T cell activation in vitro and in vivo by targeting the OX40-OX40 ligand interaction: amelioration of ongoing inflammatory bowel disease with an OX40-IgG fusion protein, but not with an OX40 ligand-IgG fusion protein" *J Immunol.* 162 (1):486-93 (Jan. 1999).

Humphreys et al., "A critical role for OX40 in T cell-mediated immunopathology during lung viral infection" *J Exp Med.* 198(8):1237-42 (Oct. 2003).

Imura et al., "OX40 expressed on fresh leukemic cells from adult T-cell leukemia patients mediates cell adhesion to vascular endothelial cells: implication for the possible involvement of OX40 in leukemic cell infiltration" *Blood* 89 (8) :2951-8 (Apr. 1997).

Imura et al., "The Human OX40/gp34 System Directly Mediates Adhesion of Activated T Cells to Vascular Endothelial Cells" *Journal of Experimental Medicine* 183 (5) :2185-2195 (May 1996).

Kjaergaard et al., "Augmentation versus inhibition: effects of conjunctional OX-40 receptor monoclonal antibody and IL-2 treatment on adoptive immunotherapy of advanced tumor" *J Immunol.* 167 (11) :6669-77 (Dec. 2001).

Lane, "Role of OX40 signals in coordinating CD4 T cell selection, migration, and cytokine differentiation in T helper (Th)1 and Th2 cells" *J Exp Med.* 191 (2) :201-6 (Jan. 2000).

Mallett and Barclay, "A new superfamily of cell surface proteins related to the nerve growth factor receptor" *Immunol Today* 12 (7) :220-3 (Jul. 1991).

Mallett et al., "Characterization of the MRC OX40 Antigen of Activated CD4 Positive T Lymphocytes—A Molecule Related to Nerve Growth Factor Receptor" *EMBO Journal* 9 (4) :1063-1068 (Apr. 1990).

Ndhlovu et al., "Critical involvement of OX40 ligand signals in the T cell priming events during experimental autoimmune encephalomyelitis" *J Immunol.* 167 (5) :2991-9 (Sep. 2001).

Ohshima et al., "Expression and function of OX40 ligand on human dendritic cells" *J Immunol.* 159 (8) :3838-48 (Oct. 1997).

Rogers et al., "OX40 promotes Bcl-xL and Bcl-2 expression and is essential for ling-term survival of CD4 T cells" *Immunity* 15(3):445-55 (Sep. 2001).

Stuber and Strober, "The T cell-B cell interaction via OX40-OX40L is necessary for the T cell-dependent humoral immune response" *J Exp Med.* 183 (3) :979-89 (Mar. 1996).

Stuber et al., "Involvement of OX40-OX40L interactions in the intestinal manifestations of the murine acute graft-versus-host disease" *Gastroenterology* 115(5):1205-15 (Nov. 1998).

Sugamura et al., "Therapeutic targeting of the effector T-cell co-stimulatory molecule OX40" *Nat Rev Immunol.* 4 (6) :420-31 (Jun. 2004).

Takahashi et al., "OX40 stimulation by gp34/OX40 ligand enhances productive human immunodeficiency virus type 1 infection" *J Virol.* 75 (15) :6748-57 (Aug. 2001).

Takasawa et al., "Expression of gp34 (OX40 ligand) and OX40 on human T cell clones" *Jpn J Cancer Res.* 92 (4) :377-82 (Apr. 2001).

Takeda, "Distinct roles for the OX40-OX40 ligand interaction in regulatory and nonregulatory T cells" *Journal of Immunology* 172:3580-9 (2004).

Taylor et al., "Identification of a soluble OX40 isoform: development of a specific and quantitative immunoassay" *J Immunol Methods.* 255:67-72 (Sep. 2001).

Wang et al., "Characterization and functional study of five novel monoclonal antibodies against human OX40L highlight reverse signalling: enhancement of IgG production of B cells and promotion of maturation of DCs" *Tissue Antigens* 64 (5) :566-74 (Nov. 2004).

Weinberg et al., "Ox-40: life beyond the effector T cell stage" *Semin Immunol.* 10 (6) :471-80 (Dec. 1998).

Weinberg et al., "Selective depletion of myelin-reactive T cells with the anti-OX-40 antibody ameliorates autoimmune encephalomyelitis" *Nature Med.* 2 (2) :183-189 (Feb. 1996).

Weinberg, "OX40: targeted immunotherapy—implications for tempering autoimmunity and enhancing vaccines" *Trends Immunol.* 23(2):102-9 (Feb. 2002).

Wu et al., "The effect of OX40/OX40L and CD27/CD70 pathways on allogeneic islet graft rejection" *Transplant Proc.* 33 (1-2) :217-8 (Feb.-Mar. 2001).

Yoshioka et al., "Contribution of OX40/OX40 ligand interaction to the pathogenesis of rheumatoid arthritis" *Eur J Immunol.* 30(10):2815-23 (Oct. 2000).

Al-Shamkhani, A., et al., "Affinity and Kinetics of the Interaction Between Soluble Trimeric OX40 Ligand, a Member of the Tumor Necrosis Factor Superfamily, and Its Receptor OX40 on Activated T Cells" *The Journal of Biological Chemistry* 272 (8) :5275-5282 (Feb. 1997).

Compaan, D., et al., "The Crystal Structure of the Costimulatory OX40-OX40L Complex" *Structure* 14 :1321-1330 (Aug. 2006).

NCBI Database Protein, "Tumor necrosis factor ligand superfamily member 4 (OX40 ligand) (OX40L) (Glycoprotein Gp34) (TAX transcriptionally-activated glycoprotein 1) (CD252 antigen) XP002484441 Accession No. P23510" (Jun. 13, 2006).

Akiba, et al., "Critical contribution of OX40 ligand to T helper cell type 2 differentiation in experimental leishmaniasis" *Journal of Experimental Medicine* 191 (2) :375-380 (2000).

Arestides, et al., "Costimulatory molecule OX40L is critical for both Th1 and Th2 responses in allergic inflammation" *European Journal of Immunology* 32:2874-2880 (2002).

Flores-Saaib, et al., "In vivo detection of cytokine expression by in situ hybridization in an ova induced murine model of asthma" *FASEB J.*710.8:A968 (2002).

Hoshino, et al., "Critical role for OX40 ligand in the development of pathogenic Th2 cells in a murine model of asthma" *European Journal of Immunology* 33:861-869 (2003).

Ishii, et al., "OX40 (CD134) and OX40 ligand interaction plays an adjuvant role during in vivo Th2 responses" *European Journal of Immunology* 33:2372-2381 (2003).

Jember, et al., "Development of allergic inflammation in a murine model of asthma is dependent on the costimulatory receptor OX40" *Journal of Experimental Medicine* 193 (3) :387-392 (2001).

Murata, et al., "OX40L-transgenic mice develop autoimmune diseases linked to failed induction of peripheral T cell tolerance" *FASEB J.*765.3:A1064 (2002).

Salek-Ardakani, et al., "Critical involment of OX40 mediated T-cell co-stimulation in lung inflammation in a murine model of asthma" *FASEB J.*518.7:A718 (2002).

Salek-Ardakani, et al., "OX40 (CD134) controls memory T helper 2 cells that drive lung inflammation" *Journal of Experimental Medicine* 198 (2) :315-324 (2003).

Salek-Ardakani, et al., "OX40 (CD134) Costimulation controls the response of memory T cells" *FASEB J.*116.21:C214 (2003).

Seshasayee, et al., "In vivo blockade of OX40 ligand inhibits thymic stromal lymphopoietin driven atopic inflammation" *The J. of Clinical Investigation* 117 (12) :3868-3878 (2007).

Wang, et al., "OX40-OX40L interactions: a promising therapeutic target for allergic diseases" *The J. of Clinical Investigation* 117:3655-3657 (2007).

* cited by examiner

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27 | 27 | 27 | 27 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 8E12 | D | I | L | M | T | Q | T | P | L | S | L | P | V | S | L | G | D | Q | A | S | I | S | C | R | S | S | Q | S | I | V | H | G | N | G | N | T | Y | L | E | W | F | L | Q | K | P |

Contact CDR-L1: positions 30–36
Chothia CDR L1: positions 24–34
Kabat CDR L1: positions 24–34

| | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|
| 8E12 | G | Q | S | P | K | L | L | I | Y | R | V | S | N | R | F | S | G | V | P | D | R | F | S | G | S | G | S | G | T | D | F | T | L | K | I | N | R | V |

Contact CDR-L2: positions 46–52
Chothia CDR-L2: positions 50–56
Kabat CDR-L2: positions 50–56

| | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|
| 8E12 | E | A | E | D | L | G | V | Y | Y | C | F | Q | G | S | H | V | P | Y | T | F | G | G | G | T | K | V | E | I | K | R |

Contact CDR-L3: positions 89–96
Chothia CDR-L3: positions 89–97
Kabat CDR-L3: positions 89–97

Kabat# 1 2 3 4 5 6 7 8 9 10 11 12 13 14 15 16 17 18 19 20 21 22 23 24 25 26 27 28 29 30 31 32 33 34 35 36 37 38 39 40

8E12    Q V Q L Q Q P G A E L V R P G A S V K L S C K A S G Y T F T S Y N L N W V K Q R 41 42 43 44 45 46 47 48 49 50 51 52 53 54 55 56 57 58 59 60 61 62 63 64 65 66 67 68 69 70 71 72 73 74 75 76 77 78 79

8E12    P G Q G L E W I V M I D P S E H H Y N Q K F K D K A I L T V D K S S T A 80 81 82 83 84 85 86 87 88 89 90 91 92 93 94 95 96 97 98 99 100 A 101 102 103 104 105 106 107 108 109 110 111 112 113 114 115 116 117 118

8E12    Y W Q L S S L T S E D S A V Y Y C I R R G N P Y G G S H N E Y W G Q G T L V T V S S

Kabat# 1  2  3  4  5  6  7  8  9  10 11 12 13 14 15 16 17 18 19 20 21 22 23 24 25 26 27 27 27 27 27 27 28 29 30 31 32 33 34 35 36 37 38 39 40

```
Kabat#  1  2  3  4  5  6  7  8  9 10 11 12 13 14 15 16 17 18 19 20 21 22 23 24 25 26 27 28 29 30 31 32 33 34 35 36 37 38 39 40
                                                                                           |Contact CDR-H1|
                                                                                   |Chothia CDR-H1|
                                                                                            |Kabat CDR-H1|
13G5    Q  V  Q  L  Q  Q  P  G  A  E  L  V  K  P  G  T  S  V  K  L  S  C  K  A  S  G  Y  S  F  T  S  Y  W  M  H  G  V  R  Q  R 41 42 43 44 45 46 47 48 49 50 51 52 53 54 55 56 57 58 59 60 61 62 63 64 65 66 67 68 69 70 71 72 73 74 75 76 77 78 79
          |Contact CDR-H2                  |
                      |Chothia CDR-H2|
                      |Kabat CDR-H2                              |
13G5    P  G  Q  G  L  E  W  I  G  E  I  D  P  S  N  G  R  T  N  Y  N  E  K  F  K  S  K  A  T  L  T  V  D  K  S  S  S  T  A 80 81 82 83 84 85 86 87 88 89 90 91 92 93 94 95 96 97 98 99 100 a 101 102 103 104 105 106 107 108 109 110 111 112 113
                                              |Contact CDR-H3                    |
                                                     |Chothia CDR-H3        |
                                                     |Kabat CDR-H3          |
13G5    Y  I  Q  L  S  S  L  T  S  E  D  S  A  V  Y  Y  C  T  R  R  S   P  R  Y  F  D  V  W  G  A  G  T  T  L  T  V  S  S
```

ANTI-OX40L ANTIBODIES AND METHODS USING SAME

CROSS-REFERENCE TO RELATED APPLICATIONS

This application is a National Stage of International Application No. PCT/US2006/062173, filed Dec. 15, 2006, which claims priority under 35 USC §119 to U.S. Provisional Application No. 60/751,377, filed Dec. 16, 2005, the entire contents of which is hereby incorporated by reference.

FIELD OF THE INVENTION

The present invention relates generally to the fields of molecular biology. More specifically, the invention concerns anti-OX40L antibodies, and uses of same.

BACKGROUND OF THE INVENTION

Human OX40 ligand (OX40L), a membrane bound member of the tumor necrosis factor superfamily, is primarily expressed on activated antigen-presenting cells, such as dendritic cells, and to a lesser degree, B cells. See Sugamura, K et al., Nature Reviews Immunology 4:420 (2004); Weinberg A D, Trends Immunol. 23(2): 102 (2002). OX40L, also known as ACT-4 receptor, TNF4-Human, GP34 and CD134L, binds to the OX40 receptor (OX40), which is also called CD134, ACT-4, CD134 antigen, ACT35 antigen, and TNR4-Human. OX40 is a T-cell activation protein that is expressed following T-cell receptor (TCR) engagement. Engagement of CD40 by activated antigen-presenting cells increases the expression of OX40L. Engagement of OX40 by OX40L is co-stimulatory to effector T cells, and costimulation up-regulates the production of cytokines by T helper 1 and T helper 2 cells. OX40-OX40L interactions are also important for the generation of memory T cells, promoting the survival of effector T cells after antigen priming. Blocking OX40L in vivo reduced the severity of rheumatoid arthritis, experimental autoimmune disease (EAE), acute graft-verses-host disease (GVHD), inflammatory bowel disease, experimental leishmaniasis and collagen-induced arthritis in animal models. See Sugamura, K et al., Nature Reviews Immunology 4:420 (2004); Weinberg A D, Trends Immunol. 23(2): 102 (2002).

Anti-OX40L and antibodies recognizing OX40L are mentioned in, e.g. in WO 95/12673; WO 95/21915; WO 99/15200; Baum, P. R., et al., EMBO J. 13 (1994) 3992-4001; Imura, A., et al., Blood 89 (1997) 2951-2958; Imura, A., et al., J. Exp. Med. 183 (1996) 2185-2195; Kjaergaard, J., et al., J. Immunol. 167 (2001) 6669-6677; Lane, P., J. Exp. Med. 191 (2000) 201-206; Mallett, S., and Barclay, A. N., Immunol. Today 12 (1991) 220-223; Mallett, S., et al., EMBO J. 9 (1990) 1063-1068; Ndhlovu, L. C., et al., J. Immunol. 167 (2001) 2991-2999; Oyhshima, Y., et al., J. Immunol. 159 (1997) 3838-3848; Rogers, P. R., et al., Immunity 15 (2001) 445-455; Stüber, E., and Strober, W., J. Exp. Med. 183 (1996) 979-989; Stüber, E., et al., Gastroenterology 115 (1998) 1205-1215; Takahashi, &., et al., J. Virol. 75 (2001) 6748-6757; Takasawa, N., et al., Jpn. J. Cancer Res. 92 (2001) 377-382; Taylor, L., and Schwarz, H., J. Immunol. Meth. 255 (2001) 67-72; Weinberg, A. D., et al., Nature Medicine 2 (1996) 183-189; Weinberg, A. D., et al., Semin. Immunol. 10 (1998) 471-480; Weinberg, A. D., Trends Immunol. 23 (202) 102-109; Wu, T., et al., Transplant. Proc. 33 (2001) 217-218; Higgins, L. M., et al., J. Immunol. 162 (1999) 486-493; Yoshioka, T., et al., Eur. J. Immunol. 30 (2000) 2815-2823; and Wang, Q., et al. Tissue Antigens 64:566-574 (2004).

Mouse anti-human OX40L antibodies are commercially available from MBL International Corp. (TAG-34) and R and D Corp (clones 159403 and 159408).

It is clear that there continues to be a need for agents that have clinical attributes that are optimal for development as therapeutic agents. The invention described herein meets this need and provides other benefits.

All references cited herein, including patent applications and publications, are incorporated by reference in their entirety.

SUMMARY OF THE INVENTION

The invention is in part based on the identification of a variety of OX40L binding agents (such as antibodies, and fragments thereof). OX40L presents as an important and advantageous therapeutic target, and the invention provides compositions and methods based on binding OX40L. OX40L binding agents of the invention, as described herein, provide important therapeutic and diagnostic agents for use in targeting pathological conditions associated with expression and/or activity of the OX40L-OX40 receptor pathways. Accordingly, the invention provides methods, compositions, kits and articles of manufacture related to OX40L binding.

In one aspect, the invention provides an isolated anti-OX40L antibody, wherein a full length IgG form of the antibody specifically binds human OX40L with a binding affinity of about 10 nM or better. As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. Any of a number of assays known in the art, including those described herein, can be used to obtain binding affinity measurements, including, for example, Biacore, radioimmunoassay (RIA) and ELISA.

In one aspect, the invention provides an isolated antibody that binds an OX40 receptor binding region of OX40L. In some embodiments, the isolated antibody binds a polypeptide comprising, consisting of or consisting of the human OX40L extracellular domain.

In one aspect, the invention provides an isolated anti-OX40L antibody that competes with OX40 receptor for binding of OX40L.

In one aspect, the invention provides an isolated anti-OX40L antibody that inhibits, reduces, and/or blocks OX40L activity.

In one aspect, the invention provides an anti-OX40L antibody that inhibits, reduces, and/or blocks T cell proliferation.

In one aspect, the invention provides an anti-OX40L antibody that inhibits, reduces, and/or blocks survival of activated T cells.

In one aspect, the invention provides an anti-OX40L antibody that inhibits, reduces, and/or blocks secretion of IL-2 from T memory cells.

In one aspect, the invention provides an anti-OX40L antibody comprising: at least one, two, three, four, five, and/or six hypervariable region (HVR) sequences selected from the group consisting of: RSSQSIVHGNGNTYLE (SEQ ID NO:1), RSSQSPVHSNGNTYLH (SEQ ID NO:2), RVSNRFS (SEQ ID NO:3), KVSNRFS (SEQ ID NO:4), FQGSHVPYT (SEQ ID NO:5), SQSTHIPWT (SEQ ID NO:6), SYWLN (SEQ ID NO:7), SYWMH (SEQ ID NO:8), MIDPSDSETHYNQVFKD (SEQ ID NO:9), EIDPSNGRT- NYNEKFKS (SEQ ID NO:10), GRGNFYGGSHAMEY (SEQ ID NO:11), and ERSPRYFDV (SEQ ID NO:12).

In one aspect, the invention provides an anti-OX40L antibody comprising: at least one, two, three, four, five, and/or six hypervariable region (HVR) sequences selected from the group consisting of: (a) HVR-L1 comprising sequence RSSQSIVHGNGNTYLE (SEQ ID NO:1) or RSSQSPVHSNGNTYLH (SEQ ID NO:2); (b) HVR-L2 comprising sequence RVSNRFS (SEQ ID NO:3) or KVSNRFS (SEQ ID NO:4); (c) HVR-L3 comprising sequence FQGSHVPYT (SEQ ID NO:5) or SQSTHIPWT (SEQ ID NO:6); (d) HVR-H1 comprising sequence SYWLN (SEQ ID NO:7) or SYWMH (SEQ ID NO:8); (e) HVR-H2 comprising sequence MIDPSDSETHYNQVFKD (SEQ ID NO:9) or EIDPSNGRTNYNEKFKS (SEQ ID NO:10); and (f) HVR-H3 comprising sequence GRGNFYGGSHAMEY (SEQ ID NO:11) or ERSPRYFDV (SEQ ID NO:12).

In one embodiment, an antibody of the invention comprises a light chain variable domain having the sequence:

```
DILMTQTPLSLPVSLGDQASISCRSSQSIVHGNGNTYLEWHLQKPGQSPKLLIYRVSNRFSGVPDRFSGSGSG    (SEQ ID NO: 13)

TDFTLKINRVEAEDLGVYYCFQGSHVPYTFGGGTKVEIKR
or

DIVMTQTPLSLPVSLGDQASMYCRSSQSPVHSNGNTYLHWYLQKPGQSPKLLIYKVSNRFSGVPDRFSGSGS    (SEQ ID NO: 14)

GTDFTLKISRVEAEDLGVYFCSQSTHIPWTFGGGTKVEIKR;
and comprises a heavy chain variable domain having the sequence:

QVQLQQPGAELVRPGASVkLSCKASGYTFTSYWLNWVKQRPGQGLEWIVMIDPSDSETHYNQVFKDKATL    (SEQ ID NO: 15)

TVDKSSSTAYMQLSSLTSEDSAVYYCIRGRGNFYGGSHAMEYWGQGTLLTVSS
or

QVQLQQPGAELVKPGTSVKLSCKASGYSFTSYWMHGVRQRPGQGLEWIGEIDPSNGRTNYNEKFKSKATL    (SEQ ID NO: 16)

TVDKSSSTAYIQLSSLTSEDSAVYYCTRERSPRYFDVWGAGTTLTVSS.
```

In one aspect, the invention provides an anti-OX40L antibody comprising: at least one, two, three, four, five, and/or six hypervariable region (HVR) sequences selected from the group consisting of: (a) HVR-L1 comprising sequence RSSQSIVHGNGNTYLE (SEQ ID NO:1) or HVR-L1 comprising sequence RSSQSPVHSNGNTYLH (SEQ ID NO:2); (b) HVR-L2 comprising sequence RVSNRFS (SEQ ID NO:3) or HVR-L2 comprising sequence KVSNRFS (SEQ ID NO:4); (c) HVR-L3 comprising sequence FQGSHVPYT (SEQ ID NO:5) or HVR-L3 comprising sequence SQSTHIPWT (SEQ ID NO:6); (d) HVR-H1 comprising sequence SYWLN (SEQ ID NO:7) or HVR-H1 comprising sequence SYWMH (SEQ ID NO:8); (e) HVR-H2 comprising sequence MIDPSDSETHYNQVFKD (SEQ ID NO:9) or HVR-H2 comprising sequence EIDPSNGRTNYNEKFKS (SEQ ID NO:10); and (f) HVR-H3 comprising sequence GRGNFYGGSHAMEY (SEQ ID NO:11) or HVR-H3 comprising sequence ERSPRYFDV (SEQ ID NO:12).

In one aspect, the invention provides an anti-OX40L antibody comprising: at least one, two, three, four, five, and/or six hypervariable region (HVR) sequences selected from the group consisting of: (a) HVR-L1 comprising sequence RSSQSIVHGNGNTYLE (SEQ ID NO:1); (b) HVR-L2 comprising sequence RVSNRFS (SEQ ID NO:3); (c) HVR-L3 comprising sequence FQGSHVPYT (SEQ ID NO:5); (d) HVR-H1 comprising sequence SYWLN (SEQ ID NO:7); (e) HVR-H2 comprising sequence MIDPSDSETHYNQVFKD (SEQ ID NO:9); and (f) HVR-H3 comprising sequence GRGNFYGGSHAMEY (SEQ ID NO:11).

In one embodiment, an antibody of the invention comprises a light chain comprising at least one, at least two or all three of HVR sequences selected from the group consisting of RSSQSIVHGNGNTYLE (SEQ ID NO:1), RVSNRFS (SEQ ID NO:3), and FQGSHVPYT (SEQ ID NO:5). In one embodiment, the antibody comprises light chain HVR-L1 having amino acid sequence RSSQSIVHGNGNTYLE (SEQ ID NO:1). In one embodiment, the antibody comprises light chain HVR-L2 having amino acid sequence RVSNRFS (SEQ ID NO:3). In one embodiment, the antibody comprises light chain HVR-L3 having amino acid sequence FQGSHVPYT (SEQ ID NO:5). In one embodiment, an antibody of the invention comprises a heavy chain comprising at least one, at least two or all three of HVR sequences selected from the group consisting of SYWLN (SEQ ID NO:7), MIDPSDSETHYNQVFKD (SEQ ID NO:9), and GRGNFYGGSHAMEY (SEQ ID NO:11). In one embodiment, the antibody comprises heavy chain HVR-H1 having amino acid sequence SYWLN (SEQ ID NO:7). In one embodiment, the antibody comprises heavy chain HVR-H2 having amino acid sequence MIDPSDSETHYNQVFKD (SEQ ID NO:9). In one embodiment, the antibody comprises heavy chain HVR-H3 having amino acid sequence GRGNFYGGSHAMEY (SEQ ID NO:11). In one embodiment, an antibody of the invention comprises a heavy chain comprising at least one, at least two or all three of HVR sequences selected from the group consisting of SYWLN (SEQ ID NO:7), MIDPSDSETHYNQVFKD (SEQ ID NO:9), and GRGNFYGGSHAMEY (SEQ ID NO:11) and a light chain comprising at least one, at least two or all three of HVR sequences selected from the group consisting of RSSQSIVHGNGNTYLE (SEQ ID NO:1), RVSNRFS (SEQ ID NO:3), and FQGSHVPYT (SEQ ID NO:5).

In one embodiment, an antibody of the invention comprises a light chain variable domain having the sequence:

```
DILMTQTPLSLPVSLGDQASISCRSSQSIVHGNGNTYLEWHLQKPGQSPKLLIYRVSNRFSGVPDRFSGSGSG    (SEQ ID NO: 13)

TDFTLKINRVEAEDLGVYYCFQGSHVPYTFGGGTKVEIKR.
```

In one embodiment, an antibody of the invention comprises a heavy chain variable domain having the sequence:

QVQLQQPGAELVRPGASVkLSCKASGYTFTSYWLNWVKQRPGQGLEWIVMIDPSDSETHYNQVFKDKATL (SEQ ID NO: 15)

TVDKSSSTAYMQLSSLTSEDSAVYYCIRGRGNFYGGSHAMEYWGQGTLLTVSS.

In one embodiment, an antibody of the invention comprises a light chain variable domain having the sequence:

DILMTQTPLSLPVSLGDQASISCRSSQSIVHGNGNTYLEWHLQKPGQSPKLLIYRVSNRESGVPDRFSGSGSG (SEQ ID NO: 13)

TDFTLKINRVEAEDLGVYYCFQGSHVPYTFGGGTKVEIKR;
and comprises a heavy chain variable domain having the sequence:

QVQLQQPGAELVRPGASVKLSCKASGYTFTSYWLNWVKQRPGQGLEWIVMIDPSDSETHYNQVFKDKATL (SEQ ID NO: 15)

TVDKSSSTAYMQLSSLTSEDSAVYYCIRGRGNFYGGSHAMEYWGQGTLLTVSS.

In one aspect, the invention provides an anti-OX40L antibody comprising: at least one, two, three, four, five, and/or six hypervariable region (HVR) sequences selected from the group consisting of: (a) HVR-L1 comprising sequence RSSQSPVHSNGNTYLH (SEQ ID NO:2); (b) HVR-L2 comprising sequence KVSNRFS (SEQ ID NO:4); (c) HVR-L3 comprising sequence SQSTHIPWT (SEQ ID NO:6); (d) HVR-H1 comprising sequence SYWMH (SEQ ID NO:8); (e) HVR-H2 comprising sequence EIDPSNGRTNYNEKFKS (SEQ ID NO:10); and (f) HVR-H3 comprising sequence ERSPRYFDV (SEQ ID NO:12).

In one embodiment, an antibody of the invention comprises a light chain comprising at least one, at least two or all three of HVR sequences selected from the group consisting of RSSQSPVHSNGNTYLH (SEQ ID NO:2), KVSNRFS (SEQ ID NO:4), and SQSTHIPWT (SEQ ID NO:6). In one embodiment, the antibody comprises light chain HVR-L1 having amino acid sequence RSSQSPVHSNGNTYLH (SEQ ID NO:2). In one embodiment, the antibody comprises light chain HVR-L2 having amino acid sequence KVSNRFS (SEQ ID NO:4). In one embodiment, the antibody comprises light chain HVR-L3 having amino acid sequence SQSTHIPWT (SEQ ID NO:6). In one embodiment, an antibody of the invention comprises a heavy chain comprising at least one, at least two or all three of HVR sequences selected from the group consisting of SYWMH (SEQ ID NO:8), EIDPSNGRTNYNEKFKS (SEQ ID NO:10, and ERSPRYFDV (SEQ ID NO:12). In one embodiment, the antibody comprises heavy chain HVR-H1 having amino acid sequence SYWMH (SEQ ID NO:8). In one embodiment, the antibody comprises heavy chain HVR-H2 having amino acid sequence EIDPSNGRTNYNEKFKS (SEQ ID NO:10. In one embodiment, the antibody comprises heavy chain HVR-H3 having amino acid sequence ERSPRYFDV (SEQ ID NO:12). In one embodiment, an antibody of the invention comprises a heavy chain comprising at least one, at least two or all three of HVR sequences selected from the group consisting of SYWMH (SEQ ID NO:8), EIDPSNGRTNYNEKFKS (SEQ ID NO:10, and ERSPRYFDV (SEQ ID NO:12) and a light chain comprising at least one, at least two or all three of HVR sequences selected from the group consisting of RSSQSPVHSNGNTYLH (SEQ ID NO:2), KVSNRFS (SEQ ID NO:4), and SQSTHIPWT (SEQ ID NO:6).

In one embodiment, an antibody of the invention comprises a light chain variable domain having the sequence:

DIVMTQTPLSLPVSLGDQASMYCRSSQSPVHSNGNTYLHWYLQKPGQSPKLLIYKVSNRFSGVPDRFSGSGS (SEQ ID NO: 14)

GTDFTLKISRVEAEDLGVYFCSQSTHIPWTFGGGTKVEIKR.

In one embodiment, an antibody of the invention comprises a heavy chain variable domain having the sequence:

QVQLQQPGAELVKPGTSVKLSCKASGYSFTSYWMHGVRQRPGQGLEWIGEIDPSNGRTNYNEKFKSKATL (SEQ ID NO: 16)

TVDKSSSTAYIQLSSLTSEDSAVYYCTRERSPRYFDVWGAGTTLTVSS.

In one embodiment, an antibody of the invention comprises a light chain variable domain having the sequence:

DIVMTQTPLSLPVSLGDQASMYCRSSQSPVHSNGNTYLHWYLQKPGQSPKLLIYKVSNRFSGVPDRFSGSGS (SEQ ID NO: 14)

GTDFTLKISRVEAEDLGVYFCSQSTHIPWTFGGGTKVEIKR;
and comprises a heavy chain variable domain having the sequence:

QVQLQQPGAELVKPGTSVKLSCKASGYSFTSYWMHGVRQRPGQGLEWIGEIDPSNGRTNYNEKFKSKATL (SEQ ID NO: 16)

TVDKSSSTAYIQLSSLTSEDSAVYYCTRERSPRYFDVWGAGTTLTVSS.

As is known in the art, and as described in greater detail hereinbelow, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below).

In some embodiments, the antibody is a monoclonal antibody. In some embodiments, the antibody is a polyclonal antibody. In some embodiments, the antibody is selected from the group consisting of a chimeric antibody, an affinity matured antibody, a humanized antibody, and a human antibody. In some embodiments, the antibody is an antibody fragment. In some embodiments, the antibody is a Fab, Fab', Fab'-SH, F(ab')$_2$, or scFv.

In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g. obtained by mutagenesis (e.g., phage display screening, etc.). In one embodiment, a chimeric antibody of the invention has murine V regions and human C region. In one embodiment, the murine light chain V region is fused to a human kappa light chain. In one embodiment, the murine heavy chain V region is fused to a human IgG1 C region.

Humanized antibodies of the invention include those that have amino acid substitutions in the FR and affinity maturation variants with changes in the grafted CDRs. The substituted amino acids in the CDR or FR are not limited to those present in the donor or recipient antibody. In other embodiments, the antibodies of the invention further comprise changes in amino acid residues in the Fc region that lead to improved effector function including enhanced CDC and/or ADCC function and B-cell killing. Other antibodies of the invention include those having specific changes that improve stability. In other embodiments, the antibodies of the invention comprise changes in amino acid residues in the Fc region that lead to decreased effector function, e.g. decreased CDC and/or ADCC function and/or decreased B-cell killing. In some embodiments, the antibodies of the invention are characterized by decreased binding (such as absence of binding) to human complement factor C1q and/or human Fc receptor on natural killer (NK) cells. In some embodiments, the antibodies of the invention are characterized by decreased binding (such as the absence of binding) to human FcγRI, FcγRIIA, and/or FcγRIIIA. In some embodiments, the antibodies of the invention is of the IgG class (e.g., IgG1 or IgG4) and comprises at least one mutation in E233, L234, G236, D265, D270, N297, E318, K320, K322, A327, A330, P331 and/or P329 (numbering according to the EU index). In some embodiments, the antibodies comprise the mutation L234A/L235A or D265A/N297A.

In one aspect, the invention provides anti-OX40L polypeptides comprising any of the antigen binding sequences provided herein, wherein the anti-OX40L polypeptides specifically bind to OX40L.

In one aspect, the invention provides an immunoconjugate (interchangeably termed "antibody drug conjugate" or "ADC") comprising any of the anti-OX40L antibodies disclosed herein conjugated to an agent, such as a drug.

The antibodies of the invention bind (in some embodiments, specifically bind) OX40L, and in some embodiments, may modulate one or more aspects of OX40L-associated effects, including but not limited to OX40L activation, OX40L downstream molecular signaling, OX40 receptor activation, OX40 receptor downstream molecular signaling, disruption of OX40 receptor binding to OX40L, OX40L multimerization, and/or disruption of any biologically relevant OX40L and/or OX40 receptor biological pathway, and/or treatment and/or prevention of an immune disorder (such as asthma, atopic dermatitis, allergic rhinitis, inflammatory bowel disease, multiple sclerosis, graft verses host disease (GVHD), and/or systemic lupus erythematosus); and/or treatment or prevention of a disorder associated with OX40L expression and/or activity (such as increased OX40L expression and/or activity). In some embodiments, the antibody of the invention specifically binds to OX40L. In some embodiments, the antibody specifically binds to an OX40 receptor binding region of OX40L. In some embodiments, the isolated antibody binds a polypeptide comprising, consisting of or consisting essentially of the human OX40L extracellular domain. In some embodiments, the antibody specifically binds OX40L with a Kd of about 1 nM or stronger. In some embodiments, the antibody specifically binds OX40L with a Kd of about 10 nM or stronger. In some embodiments, the antibody of the invention reduces, inhibits, and/or blocks OX40L activity in vivo and/or in vitro. In some embodiments, the antibody competes with Ox40L for binding with OX40 receptor (reduces and/or blocks OX40 receptor binding to OX40L).

In one aspect, the invention provides use of an antibody of the invention in the preparation of a medicament for the therapeutic and/or prophylactic treatment of a disorder, such as an immune disorder. In some embodiments, the disorder is an autoimmune disorder. In some embodiments, the disorder is asthma, atopic dermatitis, allergic rhinitis, inflammatory bowel disease, multiple sclerosis, GVHD, and/or systemic lupus erythematosus. In some embodiments, the disorder is a disease associated with virus, bacteria or other infectious agent, for example virus-induced immunopathology, e.g., pathology induced by infection with influenza or RSV or related viruses, e.g., in the lung. See generally US2005/0069548 A1. In some embodiments, the disorder is arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), autoimmune lymphoproliferative disease, inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, hives, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, graft-versus-host disease, angioedema such as hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, food allergies, drug allergies, insect allergies, rare allergic disorders such as mastocytosis, allergic reaction, eczema including allergic or atopic eczema, asteatotic eczema, dyshidrotic eczema, and vesicular palmoplantar eczema, asthma such as asthma bronchiale, bronchial asthma, autoimmune asthma, allergic asthma, and pediatric asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, SLE, such as cutaneous SLE or subacute cutaneous SLE, neonatal lupus syndrome (NLE), and lupus erythematosus disseminatus, juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia(s), cytopenias such as pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, motoneuritis, allergic neuritis, Behçet's disease/syndrome, Castleman's syndrome, Goodpasture's syndrome, Reynaud's syndrome, Sjögren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury due to an autoimmune condition, preeclampsia, an immune complex disorder such as immune complex nephritis, antibody-mediated nephritis, neuroinflammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs NSIP, Guillain-Barré syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis. Other examples, which in some cases encompass those listed above, include but are not limited to autoimmune rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteritis), autoimmune neurological disorders. (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant. GVHD, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)).

In one aspect, the invention provides compositions comprising one or more antibodies of the invention and a carrier. In one embodiment, the carrier is pharmaceutically acceptable.

In one aspect, the invention provides nucleic acids encoding an anti-OX40L antibody of the invention.

In one aspect, the invention provides vectors comprising a nucleic acid of the invention.

In one aspect, the invention provides compositions comprising one or more nucleic acid of the invention and a carrier. In one embodiment, the carrier is pharmaceutically acceptable.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods of making an antibody of the invention. For example, the invention provides methods of making an anti-OX40L antibody (which, as defined herein includes full length and fragments thereof), said method comprising expressing in a suitable host cell a recombinant vector of the invention encoding said antibody, and recovering said antibody.

In one aspect, the invention provides an article of manufacture comprising a container; and a composition contained within the container, wherein the composition comprises one or more anti-OX40L antibodies of the invention. In one embodiment, the composition comprises a nucleic acid of the invention. In one embodiment, a composition comprising an antibody further comprises a carrier, which in some embodiments is pharmaceutically acceptable. In one embodiment, an article of manufacture of the invention further comprises instructions for administering the composition (for e.g., the antibody) to a subject (such as instructions for any of the methods described herein).

In one aspect, the invention provides a kit comprising a first container comprising a composition comprising one or more anti-OX40L antibodies of the invention; and a second container comprising a buffer. In one embodiment, the buffer is pharmaceutically acceptable. In one embodiment, a composition comprising an antibody further comprises a carrier, which in some embodiments is pharmaceutically acceptable. In one embodiment, a kit further comprises instructions for administering the composition (for e.g., the antibody) to a subject.

In one aspect, the invention provides use of an anti-OX40L antibody of the invention in the preparation of a medicament for the therapeutic and/or prophylactic treatment of a disorder, such as an immune disorder. In some embodiments, the disorder is an autoimmune disorder. In some embodiments, the disorder is asthma, atopic dermatitis, allergic rhinitis, inflammatory bowel disease, multiple sclerosis, GVHD, and/or systemic lupus erythematosus.

In one aspect, the invention provides use of a nucleic acid of the invention in the preparation of a medicament for the therapeutic and/or prophylactic treatment of a disorder, such as an immune disorder. In some embodiments, the disorder is an autoimmune disorder. In some embodiments, the disorder is asthma, atopic dermatitis, allergic rhinitis, inflammatory bowel disease, multiple sclerosis, GVHD, and/or systemic lupus erythematosus.

In one aspect, the invention provides use of an expression vector of the invention in the preparation of a medicament for the therapeutic and/or prophylactic treatment of a disorder, such as an immune disorder. In some embodiments, the disorder is an autoimmune disorder. In some embodiments, the disorder is asthma, atopic dermatitis, allergic rhinitis, inflammatory bowel disease, multiple sclerosis, GVHD and/or systemic lupus erythematosus.

In one aspect, the invention provides use of a host cell of the invention in the preparation of a medicament for the therapeutic and/or prophylactic treatment of a disorder, such as an immune disorder. In some embodiments, the disorder is an autoimmune disorder. In some embodiments, the disorder is asthma, atopic dermatitis, allergic rhinitis, inflammatory bowel disease, multiple sclerosis, GVHD and/or systemic lupus erythematosus.

In one aspect, the invention provides use of an article of manufacture of the invention in the preparation of a medicament for the therapeutic and/or prophylactic treatment of a disorder, such as an immune disorder. In some embodiments, the disorder is an autoimmune disorder. In some embodiments, the disorder is asthma, atopic dermatitis, allergic rhinitis, inflammatory bowel disease, multiple sclerosis, GVHD and/or systemic lupus erythematosus.

In one aspect, the invention provides use of a kit of the invention in the preparation of a medicament for the therapeutic and/or prophylactic treatment of a disorder, such as an immune disorder. In some embodiments, the disorder is an autoimmune disorder. In some embodiments, the disorder is asthma, atopic dermatitis, allergic rhinitis, inflammatory bowel disease, multiple sclerosis, GVDH and/or systemic lupus erythematosus.

The invention provides methods and compositions useful for modulating disease states associated with expression and/or activity of OX40L, such as increased expression and/or activity or undesired expression and/or activity.

Methods of the invention can be used to affect any suitable pathological state. Exemplary disorders are described herein, and include immune disorders.

Methods of the invention can further comprise additional treatment steps. In one aspect, the invention provides methods comprising administration of an effective amount of an anti-OX40L antibody in combination with an effective amount of another therapeutic agent. For example, in one embodiment, a method further comprises a step wherein a targeted cell and/or tissue is exposed to steroid treatment. The anti-OX40L antibody can be administered serially or in combination with the other therapeutic agent that is effective for those purposes, either in the same composition or as separate compositions. The administration of the anti-OX40L antibody and the other therapeutic agent can be done simultaneously, e.g., as a single composition or as two or more distinct compositions, using the same or different administration routes. Alternatively, or additionally, the administration can be done sequentially, in any order. Alternatively, or additionally, the steps can be performed as a combination of both sequentially and simultaneously, in any order. In certain embodiments, intervals ranging from minutes to days, to weeks to months, can be present between the administrations of the two or more compositions. For example, the other therapeutic agent may be administered first, followed by the anti-OX40L antibody. However, simultaneous administration or administration of the anti-OX40L antibody first is also contemplated. In certain embodiments, intervals ranging from minutes to days, to weeks to months, can be present between the administrations of the two or more compositions.

In another aspect, the invention provides methods for detection of OX40L, the methods comprising detecting OX40L-anti-OX40L antibody complex in the sample. The term "detection" as used herein includes qualitative and/or quantitative detection (measuring levels) with or without reference to a control.

In another aspect, the invention provides methods for diagnosing a disorder associated with OX40L expression and/or activity, the methods comprising detecting OX40L-anti-OX40L antibody complex in a biological sample from a patient having or suspected of having the disorder. In some embodiments, the OX40L expression is increased expression or abnormal expression. In some embodiments, the disorder is an immune disorder In another aspect, the invention provides any of the anti-OX40L antibodies described herein, wherein the anti-OX40L antibody comprises a detectable label.

In another aspect, the invention provides a complex of any of the anti-OX40L antibodies described herein and OX40L. In some embodiments, the complex is in vivo or in vitro. In some embodiments, the anti-OX40L antibody is detectably labeled.

BRIEF DESCRIPTION OF THE FIGURES

FIGS. 1A and 1B: depict the amino acid sequences of mouse anti-human OX40L monoclonal antibody 8E12 variable regions. A, 8E12 light chain variable region (SEQ ID NO:13). B, 8E12 heavy chain variable region (SEQ ID NO:15). Amino acids are numbered according to Kabat.

FIGS. 2A and 2B: depict the amino acid sequences of mouse anti-human OX40L monoclonal antibody 13G5 variable regions. A, 13G5 light chain variable region (SEQ ID NO:14). B, 13G5 heavy chain variable region (SEQ ID NO:16). Amino acids are numbered according to Kabat.

DETAILED DESCRIPTION OF THE INVENTION

Figure 3:
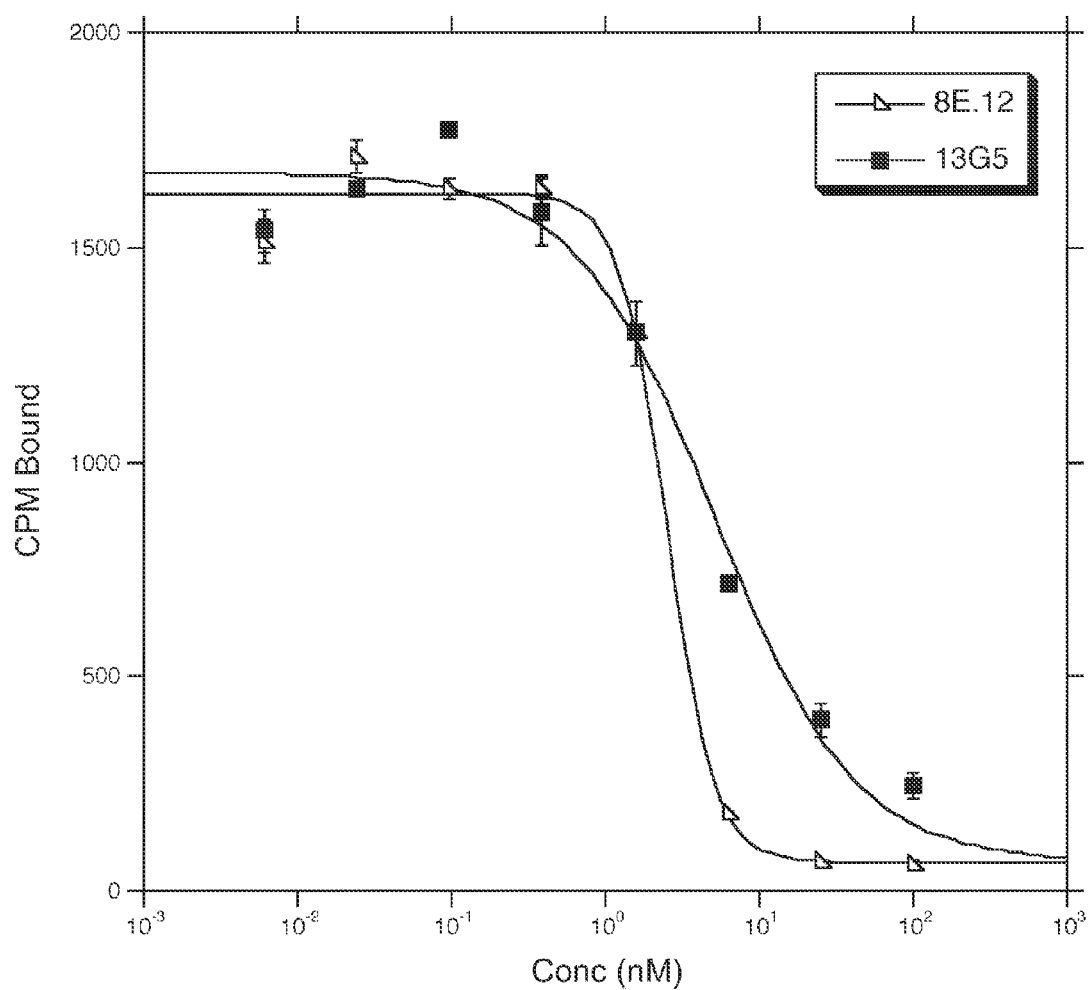
FIG. 3: graphically depicts that administration of anti-OX40L monoclonal antibodies 8E12 and 13G5 competitively inhibited binding of human OX40 receptor to human OX40L.

The invention herein provides anti-OX40L antibodies, which are useful for, e.g., treatment or prevention of disease states associated with expression and/or activity of OX40L, such as increased expression and/or activity or undesired expression and/or activity. In some embodiments, the antibodies of the invention are used to treat an immune disorder (such as asthma, atopic dermatitis, allergic rhinitis, inflammatory bowel disease, multiple sclerosis, GVHD and/or systemic lupus erythematosus).

In another aspect, the anti-OX40L antibodies of the invention find utility as reagents for detection and/or isolation of OX40L, such as detention of OX40L in various tissues and cell type.

The invention further provides methods of making anti-OX40L antibodies, polynucleotides encoding anti-OX40L antibodies, and cells comprising polynucleotides encoding anti-OX40L antibodies.

General Techniques

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

DEFINITIONS

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol Biol 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol Biol 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

An "on-rate" or "rate of association" or "association rate" or "$k_{on}$" according to this invention can also be determined with the same surface plasmon resonance technique described above using a BIAcore™-2000 or a BIAcore™-

3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) J. Mol Biol 293:865-881. However, if the on-rate exceeds $10^6 M^{-1} S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O) R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "OX40 ligand" (interchangeably termed "OX40L"), as used herein, refers, unless specifically or contextually indicated otherwise, to any native or variant (whether native or synthetic) OX40L polypeptide. The term "native sequence" specifically encompasses naturally occurring truncated or secreted forms (e.g., an extracellular domain sequence), naturally occurring variant forms (e.g., alternatively spliced forms) and naturally-occurring allelic variants. The term "wild type OX40L" generally refers to a polypeptide comprising the amino acid sequence of a naturally occurring OX40L protein. The term "wild type OX40L sequence" generally refers to an amino acid sequence found in a naturally occurring OX40L.

The term "OX40 receptor" (interchangeably termed "OX40"), as used herein, refers, unless specifically or contextually indicated otherwise, to any native or variant (whether native or synthetic) OX40 polypeptide. The term "native sequence" specifically encompasses naturally occurring truncated or secreted forms (e.g., an extracellular domain sequence), naturally occurring variant forms (e.g., alternatively spliced forms) and naturally-occurring allelic variants. The term "wild type OX40" generally refers to a polypeptide comprising the amino acid sequence of a naturally occurring OX40 protein. The term "wild type OX40 sequence" generally refers to an amino acid sequence found in a naturally occurring OX40.

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures.

Hypervariable regions may comprise "extended hypervariable regions" as follows: 24-36 (L1), 46-56 (L2) and 89-97 (L3) in the VL and 26-35 (H1), 47-66 or 49-66 or 50 to 66 (H2) and 93-101 or 93-102 (H3) in the VH. The variable domain residues are numbered according to Kabat et al., supra for each of these definitions.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). Humanized antibody as used herein is a subset of chimeric antibodies.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies*, vol. 113, Rosenburg and Moore eds., Springer-Verlag, New York, pp. 269-315 (1994).

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulates homeostasis of immunoglobulins. WO00/42072 (Presta) describes antibody variants with improved or diminished binding to FcRs. The content of that patent publication is specifically incorporated herein by reference. See, also, Shields et al. *J. Biol. Chem.* 9(2): 6591-6604 (2001).

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed.

Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

A "blocking" antibody or an "antagonist" antibody is one which inhibits or reduces biological activity of the antigen it binds. Preferred blocking antibodies or antagonist antibodies substantially or completely inhibit the biological activity of the antigen.

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include asthma, atopic dermatitis, allergic rhinitis, inflammatory bowel disease, multiple sclerosis, and systemic lupus erythematosus.

An "autoimmune disease" herein is a disease or disorder arising from and directed against an individual's own tissues or organs or a co-segregate or manifestation thereof or resulting condition therefrom. In many of these autoimmune and inflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or disorder.

An "individual" is a vertebrate, preferably a mammal, more preferably a human. Mammals include, but are not limited to, farm animals (such as cows), sport animals, pets (such as cats, dogs and horses), primates, mice and rats.

"Mammal" for purposes of treatment refers to any animal classified as a mammal, including humans, domestic and farm animals, and zoo, sports, or pet animals, such as dogs, horses, cats, cows, etc. Preferably, the mammal is human.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rnône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell (such as a cell expressing OX40L) either in vitro or in vivo. Thus, the growth inhibitory agent may be one which significantly reduces the percentage of cells (such as a cell expressing OX40L) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "Fc region-comprising polypeptide" refers to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

Compositions of the Invention and Methods of Making Same

This invention encompasses compositions, including pharmaceutical compositions, comprising an anti-OX40L antibody; and polynucleotides comprising sequences encoding an anti-OX40L antibody. As used herein, compositions comprise one or more antibodies that bind to OX40L, and/or one or more polynucleotides comprising sequences encoding one or more antibodies that bind to OX40L. These compositions may further comprise suitable carriers, such as pharmaceutically acceptable excipients including buffers, which are well known in the art.

The invention also encompasses isolated antibody and polynucleotide embodiments. The invention also encompasses substantially pure antibody and polynucleotide embodiments.

The anti-OX40L antibodies of the invention are preferably monoclonal. Also encompassed within the scope of the invention are Fab, Fab', Fab'-SH and F(ab')$_2$ fragments of the anti-OX40L antibodies provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-OX40L monoclonal antibodies of the invention can be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to OX40L generally are raised in animals by multiple subcutaneous (sc) or intraperitoneal (ip) injections of OX40L and an adjuvant. OX40L may be prepared using methods well-known in the art, some of which are further described herein. For example, recombinant production of OX40L is described below. In one embodiment, animals are immunized with a derivative of OX40L that contains the extracellular domain (ECD) of OX40L fused to the Fc portion of an immunoglobulin heavy chain. In a preferred embodiment, animals are immunized with an OX40L-IgG1 fusion protein. Animals ordinarily are immunized against immunogenic conjugates or derivatives of OX40L with monophosphoryl lipid A (MPL)/trehalose dicorynomycolate (TDM) (Ribi Immunochem. Research, Inc., Hamilton, Mont.) and the solution is injected intradermally at multiple sites. Two weeks later the animals are boosted. 7 to 14 days later animals are bled and the serum is assayed for anti-OX40L titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against OX40L. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The anti-OX40L antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-OX40L antibodies of the invention can be obtained by designing a suitable antigen screening procedure to select for the phage clone of interest followed by construction of a full length anti-OX40L antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-OX40L clones is desired, the subject is immunized with OX40L to generate an antibody response, and spleen cells and/or circulating B cells other peripheral blood lymphocytes (PBLs) are recovered for library construction. In a preferred embodiment, a human antibody gene fragment library biased in favor of anti-human OX40L clones is obtained by generating an anti-human OX40L antibody response in transgenic mice carrying a functional human immunoglobulin gene array (and lacking a functional endogenous antibody production system) such that OX40L immunization gives rise to B cells producing human antibodies against OX40L. The generation of human antibody-producing transgenic mice is described below.

Additional enrichment for anti-OX40L reactive cell populations can be obtained by using a suitable screening procedure to isolate B cells expressing OX40L-specific membrane bound antibody, e.g., by cell separation with OX40L affinity chromatography or adsorption of cells to fluorochrome-labeled OX40L followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which OX40L is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci. (USA)*, 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci. (USA)*, 86: 5728-5732 (1989). To maximize complementarity, degeneracy can be incorporated in the primers as described in Orlandi et al. (1989) or Sastry et al. (1989). Preferably, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al., *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

The antibodies produced by naive libraries (either natural or synthetic) can be of moderate affinity ($K_d^{-1}$ of about $10^6$ to $10^7 M^1$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique*, 1: 11-15 (1989)) in the method of Hawkins et al., *J. Mol. Biol.*, 226: 889-896 (1992) or in the method of Gram et al., *Proc. Natl. Acad. Sci. USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities in the $10^{-9}$ M range.

Nucleic acid sequence encoding the OX40L can be designed using the amino acid sequence of the desired region of OX40L, e.g. the extracellular domain. Alternatively, the cDNA sequence (or fragments thereof) may be used. Additional OX40L sequences are further disclosed in, e.g., SwisProt Accession Number P23510. DNAs encoding OX40L can be prepared by a variety of methods known in the art. These methods include, but are not limited to, chemical synthesis by any of the methods described in Engels et al., *Agnew. Chem. Int. Ed. Engl.*, 28: 716-734 (1989), such as the triester, phosphite, phosphoramidite and H-phosphonate methods. In one embodiment, codons preferred by the expression host cell are used in the design of the OX40L-encoding DNA. Alternatively, DNA encoding OX40L can be isolated from a genomic or cDNA library.

Following construction of the DNA molecule encoding OX40L, the DNA molecule is operably linked to an expression control sequence in an expression vector, such as a plasmid, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells. Suitable vectors for expression in prokaryotic and eukaryotic host cells are known in the art and some are further described herein. Eukaryotic organisms, such as yeasts, or cells derived from multicellular organisms, such as mammals, may be used.

Optionally, the DNA encoding OX40L is operably linked to a secretory leader sequence resulting in secretion of the expression product by the host cell into the culture medium. Examples of secretory leader sequences include stII, ecotin, lamB, herpes GD, lpp, alkaline phosphatase, invertase, and alpha factor. Also suitable for use herein is the 36 amino acid leader sequence of protein A (Abrahmsen et al., *EMBO J.*, 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ precipitation and electroporation. Successful transfection is generally recognized when any indication of the operation of this vector occurs within the host cell. Methods for transfection are well known in the art, and some are further described herein.

Transformation means introducing DNA into an organism so that the DNA is replicable, either as an extrachromosomal element or by chromosomal integrant. Depending on the host cell used, transformation is done using standard techniques appropriate to such cells. Methods for transformation are well known in the art, and some are further described herein.

Prokaryotic host cells used to produce OX40L can be cultured as described generally in Sambrook et al., supra.

The mammalian host cells used to produce OX40L can be cultured in a variety of media, which is well known in the art and some of which is described herein.

The host cells referred to in this disclosure encompass cells in in vitro culture as well as cells that are within a host animal.

Purification of OX40L may be accomplished using art-recognized methods.

The purified OX40L can be attached to a suitable matrix such as agarose beads, acrylamide beads, glass beads, cellulose, various acrylic copolymers, hydroxylmethacrylate gels, polyacrylic and polymethacrylic copolymers, nylon, neutral and ionic carriers, and the like, for use in the affinity chromatographic separation of phage display clones. Attachment of the OX40L protein to the matrix can be accomplished by the methods described in *Methods in Enzymology*, vol. 44 (1976). A commonly employed technique for attaching protein ligands to polysaccharide matrices, e.g. agarose, dextran or cellulose, involves activation of the carrier with cyanogen halides and subsequent coupling of the peptide ligand's primary aliphatic or aromatic amines to the activated matrix.

Alternatively, OX40L can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized OX40L under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci. USA*, 88: 7978-7982 (1991), or by alkali, e.g. as described in Marks et al., *J. Mol. Biol.*, 222: 581-597 (1991), or by OX40L antigen competition, e.g. in a procedure similar to the antigen competition method of Clackson et al., *Nature*, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for OX40L. However, random mutation of a selected antibody (e.g. as performed in some of the affinity maturation techniques described above) is likely to give rise to many mutants, most binding to antigen, and a few with higher affinity. With limiting OX40L, rare high affinity phage could be competed out. To retain all the higher affinity mutants, phages can be incubated with excess biotinylated OX40L, but with the biotinylated OX40L at a concentration of lower molarity than the target molar affinity constant for OX40L. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-OX40L clones may be activity selected. In one embodiment, the invention provides anti-OX40L antibodies that block the binding between an OX40 receptor and OX40L, but do not block the binding between an and a second protein. Fv clones corresponding to such anti-OX40L antibodies can be selected by (1) isolating anti-OX40L clones from a phage library as described above, and optionally amplifying the isolated population of phage clones by growing up the population in a suitable bacterial host; (2) selecting OX40L and a second protein against which blocking and non-blocking activity, respectively, is desired; (3) adsorbing the anti-OX40L phage clones to immobilized OX40L; (4) using an excess of the second protein to elute any undesired clones that recognize OX40L-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-OX40L antibody derived from a hybridoma of the invention can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA*, 81: 6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA*, 89:4285; Presta et al. (1993) *J. Immunol.*, 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-OX40L antibodies of the invention can be constructed by combining Fv clone variable domain sequence(s) selected from human-derived phage display libraries with known human constant domain sequences(s) as described above. Alternatively, human monoclonal anti-OX40L antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90: 2551 (1993); Jakobovits et al., *Nature*, 362: 255 (1993); Bruggermann et al., *Year in Immunol.*, 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal, preferably human or humanized, antibodies that have binding specificities for at least two different antigens. In the present case, one of the binding specificities is for OX40L and the other is for any other antigen. Exemplary bispecific antibodies may bind to two different epitopes of the OX40L protein. Bispecific antibodies may also be used to localize cytotoxic agents to cells which express OX40L. These antibodies possess an OX40L-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature*, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.*, 10: 3655 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fe region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of amino acid variant of the antibody alters the original glycosylation pattern of the antibody. Such altering includes deleting one or more carbohydrate moieties found in the antibody, and/or adding one or more glycosylation sites that are not present in the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US. Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. *J. Mol. Biol.* 336: 1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |

TABLE 1-continued

| Original Residue | Exemplary Substitutions | Preferred Substitutions |
| --- | --- | --- |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: Cys, Ser, Thr, Asn, Gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine. In accordance with this description and the teachings of the art, it is contemplated that in some embodiments, an antibody used in methods of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter *Nature* 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. *J. Immunol.* 164: 4178-4184 (2000).

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Screening for Antibodies with Desired Properties

The antibodies of the present invention can be characterized for their physical/chemical properties and biological functions by various assays known in the art. In some embodiments, antibodies are characterized for any one or more of binding to OX40L, reduction or blocking of OX40L activation, reduction or blocking of OX40L downstream molecular signaling, reduction or blocking of OX40 receptor activation, reduction or blocking of OX40 receptor downstream molecular signaling, reduction or blocking of OX40 binding to OX40L and/or OX40L multimerization, and/or treatment and/or prevention of an immune disorder (e.g., asthma, allergic rhinitis, atopic dermatitis, multiple sclerosis, GVHF, or systemic lupus erythematosus); and/or treatment and/or prevention of a disorder associated with OX40L expression and/or activity (such as increased OX40L expression and/or activity).

The purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the antibodies produced herein are analyzed for their biological activity. In some embodiments, the antibodies of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. Illustrative antigen binding assay are provided below in the Examples section.

In some embodiments, the invention provides anti-OX40L monoclonal antibodies that compete with antibody 8E12 and/or 13G5 antibody for binding to OX40L. Such competitor antibodies include antibodies that recognize an OX40L epitope that is the same as or overlaps with the OX40L epitope recognized by antibody 8E12 and/or 13G5. Such competitor antibodies can be obtained by screening anti-OX40L hybridoma supernatants for binding to immobilized OX40L in competition with labeled 8E12 and/or 13G5 antibody. A hybridoma supernatant containing competitor antibody will reduce the amount of bound, labeled antibody detected in the subject competition binding mixture as compared to the amount of bound, labeled antibody detected in a control binding mixture containing irrelevant (or no) antibody. Any of the competition binding assays described herein are suitable for use in the foregoing procedure.

Anti-OX40L antibodies of the invention possessing the properties described herein can be obtained by screening anti-OX40L hybridoma clones for the desired properties by any convenient method. For example, if an anti-OX40L monoclonal antibody that blocks or does not block the binding of OX40 receptor to OX40L is desired, the candidate antibody can be tested in a binding competition assay, such as a competitive binding ELISA, wherein plate wells are coated with OX40L, and a solution of antibody in an excess of OX40 receptor is layered onto the coated plates, and bound antibody is detected enzymatically, e.g. contacting the bound antibody with HRP-conjugated anti-Ig antibody or biotinylated anti-Ig antibody and developing the HRP color reaction, e.g. by developing plates with streptavidin-HRP and/or hydrogen peroxide and detecting the HRP color reaction by spectrophotometry at 490 nm with an ELISA plate reader.

If an anti-OX40L antibody that inhibits OX40L activation is desired, the candidate antibody can be testing an assay that detects OX40L pathway signaling or OX40 pathway signalling, such as an NFκB signaling assay. Such assays are known in the art.

Other functional assays to determine the inhibitory capacity of anti-OX40L antibodies are known in the art, some of which are exemplified herein.

In some embodiments, the present invention contemplates altered antibodies that possess some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

In some embodiments, the invention provides altered antibodies that possess increased effector functions and/or increased half-life.

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells:
i. Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB- strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTA(nmpc-fepE) degP41 kanR (U.S. Pat. No. 5,639,635). Other strains and derivatives thereof, such as *E. coli* 294 (ATCC 31,446), *E. coli* B, *E. coli*λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to, Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

The invention also provides immunoconjugates (interchangeably termed "antibody-drug conjugates" or "ADC"), comprising any of the anti-OX40L antibodies described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the $CD_{20}$ antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of immunoconjugates are described herein (eg., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA. 1 that binds the HER-2/neu oncogene. The cytotoxicity of the TA. 1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolastatins

In some embodiments, the immunoconjugate comprises an antibody of the invention conjugated to dolastatins or dolostatin peptidic analogs and derivatives, the auristatins (U.S. Pat.

Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983, 340, filed Nov. 5, 2004, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712, 374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I, \alpha_2^I, \alpha_3^I$, N-acetyl-yl, PSAG and $\theta^I_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-11, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as his (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab-(L-D)_p \qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Pharmaceutical Formulations

Therapeutic formulations comprising an antibody of the invention are prepared for storage by mixing the antibody having the desired degree of purity with optional physiologically acceptable carriers, excipients or stabilizers (*Remington: The Science and Practice of Pharmacy* 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine;

monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy* 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPO™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used in, for example, in vitro, ex vivo and in vivo therapeutic methods.

In one aspect, the invention provides methods for treating or preventing an immune disorder, the methods comprising administering an effective amount of an anti-OX40L antibody to a subject in need of such treatment. In some embodiments, the immune disorder is an immune disorder. In some embodiments, the disorder is an autoimmune disorder. In some embodiments, the disorder is asthma, atopic dermatitis, allergic rhinitis, inflammatory bowel disease, multiple sclerosis, GVHD, and/or systemic lupus erythematosus. In some embodiments, the disorder is a disease associated with virus, bacteria or other infectious agent. See US2005/0069548 A1.

Moreover, at least some of the antibodies of the invention can bind antigen from other species. Accordingly, the antibodies of the invention can be used to bind specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, the antibody of the invention can be used for inhibiting antigen activities by contacting the antibody with the antigen such that antigen activity is inhibited. Preferably, the antigen is a human protein molecule.

In one embodiment, an antibody of the invention can be used in a method for binding an antigen in a subject suffering from a disorder associated with increased antigen expression and/or activity, comprising administering to the subject an antibody of the invention such that the antigen in the subject is bound. Preferably, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the immunoglobulin cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

The antibodies of the invention can be used to treat, inhibit, delay progression of, prevent/delay recurrence of, ameliorate, or prevent diseases, disorders or conditions associated with expression and/or activity of one or more antigen molecules.

In certain embodiments, an immunoconjugate comprising an antibody conjugated with one or more cytotoxic agent(s) is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. In one embodiment, the cytotoxic agent targets or interferes with microtubule polymerization. Examples of such cytotoxic agents include any of the chemotherapeutic agents noted herein (such as a maytansinoid, auristatin, dolastatin, or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, steroids (such as inhalable, systemic or cutaneous steroids), chemotherapeutic agent(s) (including cocktails of chemotherapeutic agents), other cytotoxic agent(s), anti-angiogenic agent(s), cytokines, and/or growth inhibitory agent(s). Such combined therapies noted above include combined administration (where the two or more agents are included in the same or separate formulations), and separate administration, in which case, administration of the antibody of the invention can occur prior to, and/or following, administration of the adjunct therapy or therapies. The effective amounts of therapeutic agents administered in combination with an anti-EphB4 antibody will be at the physician's or veterinarian's discretion. Dosage administration and adjustment is done to achieve maximal management of the conditions to be treated. The dose will additionally depend on such factors as the type of therapeutic agent to be used and the specific patient being treated. In certain embodiments, the combination of the inhibitors potentiates the efficacy of a single inhibitor. The term "potentiate" refers to an improvement in the efficacy of a therapeutic agent at its common or approved dose.

The antibody of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of an antibody of the invention (when used alone or in combination with other agents will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody is an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

The anti-OX40L antibodies of the invention are useful in assays detecting OX40L expression (such as diagnostic or prognostic assays) in specific cells or tissues wherein the antibodies are labeled as described below and/or are immobilized on an insoluble matrix.

In another aspect, the invention provides methods for detection of OX40L, the methods comprising detecting OX40L-anti-OX40L antibody complex in the sample. The term "detection" as used herein includes qualitative and/or quantitative detection (measuring levels) with or without reference to a control.

In another aspect, the invention provides methods for diagnosing a disorder associated with OX40L expression and/or activity, the methods comprising detecting OX40L-anti-OX40L antibody complex in a biological sample from a patient having or suspected of having the disorder. In some embodiments, the OX40L expression is increased expression or abnormal (undesired) expression.

In another aspect, the invention provides any of the anti-OX40L antibodies described herein, wherein the anti-OX40L antibody comprises a detectable label.

In another aspect, the invention provides a complex of any of the anti-OX40L antibodies described herein and OX40L. In some embodiments, the complex is in vivo or in vitro. In some embodiments, the complex comprises a cancer cell. In some embodiments, the anti-OX40L antibody is detectably labeled.

Anti-OX40L antibodies can be used for the detection of OX40L in any one of a number of well known detection assay methods. For example, a biological sample may be assayed for OX40L by obtaining the sample from a desired source, admixing the sample with anti-OX40L antibody to allow the antibody to form antibody/OX40L complex with any OX40L present in the mixture, and detecting any antibody/OX40L complex present in the mixture. The biological sample may be prepared for assay by methods known in the art which are suitable for the particular sample. The methods of admixing the sample with antibodies and the methods of detecting antibody/OX40L complex are chosen according to the type of assay used. Such assays include immunohistochemistry, competitive and sandwich assays, and steric inhibition assays.

Analytical methods for OX40L all use one or more of the following reagents: labeled OX40L analogue, immobilized OX40L analogue, labeled anti-OX40L antibody, immobilized anti-OX40L antibody and steric conjugates. The labeled reagents also are known as "tracers."

The label used is any detectable functionality that does not interfere with the binding of OX40L and anti-OX40L antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include: The label used is any detectable functionality that does not interfere with the binding of OX40L and anti-OX40L antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, p-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. Nos. 3,940,475 (fluorimetry) and 3,645,090 (enzymes); Hunter et al., *Nature,* 144: 945 (1962); David et al., *Biochemistry,* 13: 1014-1021 (1974); Pain et al., *J. Immunol. Methods,* 40: 219-230 (1981); and Nygren, *J. Histochem. and Cytochem.,* 30: 407-412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology,* ed. J. J. Langone and H. Van Vunakis, Vol. 73 (Academic Press, New York, N.Y., 1981), pp. 147-166.

Immobilization of reagents is required for certain assay methods. Immobilization entails separating the anti-OX40L antibody from any OX40L that remains free in solution. This conventionally is accomplished by either insolubilizing the anti-OX40L antibody or OX40L analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-OX40L antibody or OX40L analogue afterward, e.g., by immunoprecipitation.

The expression of proteins in a sample may be examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods. For sample preparation, a tissue or cell sample from a mammal (typically a human patient) may be used. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology. One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used.

IHC may be performed in combination with additional techniques such as morphological staining and/or fluorescence in-situ hybridization. Two general methods of IHC are available; direct and indirect assays. According to the first assay, binding of antibody to the target antigen (e.g., OX40L) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

Aside from the sample preparation procedures discussed above, further treatment of the tissue section prior to, during or following IHC may be desired, For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g. using a microscope, and staining intensity criteria, routinely used in the art, may be employed.

Other assay methods, known as competitive or sandwich assays, are well established and widely used in the commercial diagnostics industry.

Competitive assays rely on the ability of a tracer OX40L analogue to compete with the test sample OX40L for a limited number of anti-OX40L antibody antigen-binding sites. The anti-OX40L antibody generally is insolubilized before or after the competition and then the tracer and OX40L bound to the anti-OX40L antibody are separated from the unbound tracer and OX40L. This separation is accomplished by decanting (where the binding partner was preinsolubilized) or by centrifuging (where the binding partner was precipitated after the competitive reaction). The amount of test sample OX40L is inversely proportional to the amount of bound tracer as measured by the amount of marker substance. Dose-response curves with known amounts of OX40L are prepared and compared with the test results to quantitatively determine the amount of OX40L present in the test sample. These assays are called ELISA systems when enzymes are used as the detectable markers.

Another species of competitive assay, called a "homogeneous" assay, does not require a phase separation. Here, a conjugate of an enzyme with the OX40L is prepared and used such that when anti-OX40L antibody binds to the OX40L the presence of the anti-OX40L antibody modifies the enzyme activity. In this case, the OX40L or its immunologically active fragments are conjugated with a bifunctional organic bridge to an enzyme such as peroxidase. Conjugates are selected for use with anti-OX40L antibody so that binding of the anti-OX40L antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small OX40L fragment so that antibody to hapten is substantially unable to bind the conjugate at the same time as anti-OX40L antibody. Under this assay procedure the OX40L present in the test sample will bind anti-OX40L antibody, thereby allowing anti-hapten to bind the conjugate, resulting in a change in the character of the conjugate hapten, e.g., a change in fluorescence when the hapten is a fluorophore.

Sandwich assays particularly are useful for the determination of OX40L or anti-OX40L antibodies. In sequential sandwich assays an immobilized anti-OX40L antibody is used to adsorb test sample OX40L, the test sample is removed as by washing, the bound OX40L is used to adsorb a second, labeled anti-OX40L antibody and bound material is then separated from residual tracer. The amount of bound tracer is directly proportional to test sample OX40L. In "simultaneous" sandwich assays the test sample is not separated before adding the labeled anti-OX40L. A sequential sandwich assay using an anti-OX40L monoclonal antibody as one antibody and a polyclonal anti-OX40L antibody as the other is useful in testing samples for OX40L.

The foregoing are merely exemplary detection assays for OX40L. Other methods now or hereafter developed that use anti-OX40L antibody for the determination of OX40L are included within the scope hereof, including the bioassays described herein.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition(s) effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as asthma. Moreover, the article of manufacture may comprise (a) a first container with a composition contained therein, wherein the composition comprises an antibody of the invention; and (b) a second container with a composition contained therein. The article of manufacture in this embodiment of the invention may further comprise a package insert indicating that the first and second antibody compositions can be used to treat a particular condition, e.g. asthma. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Example 1

Preparation of Anti-OX40L Mouse Monoclonal Antibodies 8E12 and 13G5

Antibodies to the extracellular sequence of human OX40L were prepared as follows. Five Balb/c mice (Charles River Laboratories, Wilmington, Del.) were hyperimmunized with recombinant human OX40L-flag polypeptide (human OX40 ligand extracellular domain fused to the flag peptide and expressed from CHO cells, Genentech, Inc., South San Francisco, Calif.), in Ribi adjuvant (Ribi Immunochem Research, Inc., Hamilton, Mo.). B-cells from mice demonstrating high anti-OX40L antibody titers were fused with mouse myeloma cells (pu1.Anan.22.4, Genentech, Inc., South San Francisco, Calif.). After several days, the supernatants were harvested and screened for antibody production by direct enzyme-linked immunosorbent assay (ELISA). IgG from the growth conditioned media of positive clones was purified by Protein A affinity chromatography (Pharmacia fast protein liquid chromatography (Pharmacia, Uppsala, Sweden). The purified antibody preparations were sterile filtered (0.2-$\mu$m pore size; Nalgene, Rochester N.Y.) and stored at 4° C. in phosphate buffered saline (PBS).

Flow cytometry based assays were performed with the growth-conditioned media of ELISA positive clones to screen for monoclonal antibodies that compete with recombinant OX40R-Fc (human OX40 receptor fused to the Fc fragment of IgG$_1$ expressed from CHO cells, Genentech, Inc.) for binding to human OX40L expressed on CHO cells. CHO-OX40L cells were pre-incubated with OX40R-Fc followed by the addition of the growth-conditioned media. After incubating, the cells were washed in phosphate buffer saline and then stained with phycoerytherin-conjugated anti-murine IgG to detect the amount of bound murine anti-human OX40L monoclonal antibodies. The mean fluorescence index (MFI) was determined. Monoclonal antibodies (Mabs) designated 8E12 and 13G5 performed well in these assays.

Total RNA was extracted from hybridoma cells producing the 8E12 and 13G5 antibodies, using standard methods. The variable light (VL) and variable heavy (VH) domains were amplified using RT-PCR with degenerate primers to heavy and light chain as follows. The forward primers were specific for the N-terminal amino acid sequence of the VL and VH region. The LC and HC reverse primers were designed to anneal to a region in the constant light (CL) and constant heavy domain 1 (CH1), respectively, which are highly conserved across species. Amplified VL and VH regions were cloned into mammalian expression vectors, and the polynucleotide sequence of the inserts was determined using routine sequencing methods. The 8E12 VL and VH amino acid sequences are shown in FIG. 1. The 13G5 VL and VH amino acid sequences are shown in FIG. 3.

Example 2

ELISA Analysis of Mab 8E12 and 13G5 Binding to OX40L Protein

Competition ELISA analysis was conducted as follows to examine binding of anti-OX40L Mabs 8E12 and 13G5 to OX40L in solution, and to examine binding to cell-surface expressed OX40L. In some experiments, maxiSorp 96-well microwell plates (Nunc, Roskilde, Denmark) were coated overnight at 4° C. with 2 ug/ml anti-FlagM2 antibody (Sigma) in 50 mM carbonate buffer, pH 9.6. Plates were washed with PBS containing 0.05% polysorbate 20 and blocked with 0.5% bovine serum albumin, 10 ppm Proclin 300 (Supelco, Bellefonte, Pa.) in PBS at room temperature for 1 h. Plates were washed and 0.5 ug/ml of human OX40L ECD-Flag polypeptide was added. After a one-hour incubation, plates were washed. A mixture of human OX40-IgG-bio and serial dilutions of antibodies in PBS containing 0.5% bovine serum albumin, 0.05% polysorbate 20, 10 ppm Proclin 300 was added. The plates were incubated for 2 h at room temperature and washed. Bound human OX40-IgG-bio was detected by adding streptavidin-HRP (Amdex, Copenhagen, Denmark) followed by 3,3',5,5'-tetramethyl benzidine (Kirkegaard & Perry Laboratories, Gaithersburg, Md.) as the substrate. Plates were developed and the reaction was stopped by adding 1 M phosphoric acid. Absorbance was read at 450 nm on a Titertek stacker reader (ICN, Costa Mesa, Calif.). The titration curves were fit using a four parameter regression curve fitting program (KaleidaGraph, Synergy software, Reading, Pa.). Anti-OX40L Mabs 8E12 and 13G5 bound human OX40L with an approximate EC50 of 1.4 nM and 1.1 nM, respectively. In some experiments, the assay was carried out similarly as above, except that ELISA plates were coated with 0.5 ug/ml human OX40-IgG, a mixture of human OX40-Flag and serial dilutions of antibodies were incubated on the plates, and bound human OX40-Flag was detected using anti-Flag-bio antibody followed by streptavidin-HRP. Anti-OX40L Mabs 8E12 and 13G5 bound human OX40L with an approximate EC50 of 1.9 nM and 0.46 nM, respectively.

In other experiments, CHO cells expressing full-length human OX40L were grown in 50:50 F12/DMEM medium supplemented with 2 mM L-glutamine, 100 units/ml penicillin, 100 ug/ml streptomycin (supplemented medium), and 5% FBS (Gibco BRL Life Technologies, Gaithersburg, Md.) (growth medium) in a humidified 5% $CO_2$ incubator at 37° C. Cells were detached from culture plates using Accutase (ICN) and added to 96 well microwell plates at 300,000 cells/well. A mixture of human OX40-IgG and serial dilutions of antibodies in growth medium was added to the plates. After a one-hour incubation on ice, cells were washed by centrifuging the plates and removing the supernatant. Bound human OX40-IgG was detected using anti-Fc-HRP. EC50s were estimated to be 20 and 130 nM for 8E12 and 13G5, respectively. In some experiments, human OX40-IgG-bio was used instead of human OX40-IgG. Bound human OX40-IgG-bio was detected using streptavidin-HRP. Plates were developed and read as described above. Mabs 8E12 and 13G5 bound human OX40L with an approximate EC50 of about 11 nM and 60 nM, respectively.

These analyses demonstrated that Mabs 8E12 and 13G5 bound human OX40L in solution and human OX40L expressed on CHO cells.

To determine whether Mabs 8E12 and 13G5 bound mouse OX40L, ELISA plates were coated with mouse OX40L. Serial dilutions of 8E12 or 13G5 (0.004-4 ug/ml) were added. Goat anti-mouse Fc-HRP was used for detection. No binding was observed. In a different format, ELISA plates were coated with 8E12 or 13G5. Serial dilutions of mouse OX40L-Flag were added. Biotinylated anti-Flag followed by streptavidin-HRP was used for detection. No binding was observed.

Example 3

Analysis of Mab 8E12 and 13G5 Using Surface Plasmon Resonance

Binding kinetics of mouse anti-OX40L antibodies to human OX40L were measured by surface plasmon resonance using Pharmacia BIAcore® 3000 (BIAcore AB, Uppsala, Sweden) at room temperature (Karlsson et al., 1994; Morton & Myszka, 1998). Anti-Flag antibody (anti-FlagM2, Sigma, St. Louis, Mo.) was immobilized to the sensor chip (CM5) through primary amine groups. A high flow rate was used in order to minimize mass transport effects. The carboxymethylated sensor chip surface matrix was activated by injecting 20 ul of a mixture of 0.025 M N-hydroxysuccinimide and 0.1 M N-ethyl-N'(dimethylaminopropyl) carbodiimide at 5 ul/min. 7 ul of 50 ug/ml anti-Flag in 10 mM sodium acetate, pH 4.5, were injected at 5 ul/min twice. After coupling, unoccupied sites on the chip were blocked by injecting 20 ul of 1M ethanolamine, pH 8.5. The running buffer was PBS containing 0.05% polysorbate 20. 5 ul of 4 ug/ml OX40L-Flag were injected at 30 ul/min to bind OX40-Flag to the anti-Flag on the chip. For kinetic measurements, two-fold serial dilutions (6.2-50 nM) of mouse anti-human OX40 antibodies 8E12 (PUR 9333) and 13G5 (PUR 9306) in running buffer were injected over flow cell for 2 minutes at a flow rate of 30 ul/min and the bound anti-OX40L antibody was allow to dissociate for 20 minutes. The binding surface was regenerated by injecting 30 ul of 10 mM glycine.HCl (pH 1.5). A flow cell, which had anti-Flag antibody immobilized but did not receive OX40L-Flag, was used as a reference cell. Data were analyzed using a 1:1 binding model using global fitting. The association and dissociation rate constants were fitted simultaneously (BIAevaluation software).

The apparent on-rate constants were $2.6 \times 10^6$ and $4.8 \times 10^5$ (1/Ms) for 8E12 and 13G5 IgG antibodies, respectively. Due to very slow off-rate kinetics, the off-rate constants could not be determined ($<5 \times 10^6$/s). The calculated apparent Kd values were <0.019 nM and <0.010 nM for 8E12 and 13G5 IgG antibodies, respectively.

Example 4

Anti-OX40L Antibodies 8E12 and 13G5 Recognized Different Binding Determinants on OX40L Scatchard binding experiments were performed to determine if anti-OX40L mAbs 8E12 and 13G5 compete with each other for binding similar or overlapping epitopes on CHO cells expressing human OX40L, and to determine the binding affinity of the antibodies. 50 ug of anti-OX40L murine monoclonal antibodies 8E12 and 13G5 were iodinated using a standard lactoperoxidase method. Antibodies 8E12 and 13G5 were serially diluted 1:4 in media buffer (Dubeccos F12: DMEM, 1% bovine serum albumin, 0.05% sodium azide and 25 mM Hepes buffer pH 7.2) starting at an initial concentration of 200 nM. Two sets of dilution series (50 uL) were performed in duplicate in a 96 microwell plate. Wells from each set of dilutions received 50 uL of either iodinated 8E12 or 13G5 (0.25 nM final concentration). The plate was mixed and then the entire mixture was transferred to a 96 well tissue culture plate containing 30,000 OX40L-expressing CHO cells per well which had been plated out the previous day. The plates were covered and incubated overnight at 4° C. The next day the wells (containing cells) were aspirated and washed twice with media buffer. 200 uL of 1N NaOH was added to each well to lyse the cells, shaken for 10 minute, and then transferred to a 96 well microtube. Each tube was counted in a Wallac gamma scintillation counter. The counts bound along with antibody concentrations were entered in the Scatchard analysis program New Ligand to plot the bound versus bound/free and to determine the binding affinity and receptor concentration. For competition experiments, the data was collected and plotted using Kaleidagraph. Curves were drawn using a 4-parameter fit.

Mab 8E12 bound human OX40L with a Kd of 0.92 nM. Mab 13G5 bound human OX40L with a Kd of 1.09 nM. 8E12 and 13G5 did not compete with each other for binding OX40L expressed on CHO cells, indicating that anti-OX40L monoclonal antibodies 8E12 and 13G5 recognized different human OX40L binding determinates.

Example 5

Anti-OX40L Antibodies Inhibited the Interaction of Human OX40L and Human OX40

Competitive binding experiments were performed to determine if anti-OX40L mAbs 8E12 and 13G5 competed with iodinated OX40-Fc (extracellular domain of OX40 receptor fused to Fc domain) for binding to OX40L expressed on CHO cells. 50 ug of OX40L-Fc ligand was iodinated using a standard lactoperoxidase method. Antibodies 8E12 and 13G5 were serially diluted 1:4 in media buffer (Dubeccos F12: DMEM, 1% bovine serum albumin, 0.05% sodium azide and 25 mM Hepes buffer pH 7.2) starting at an initial concentration of 200 nM. Dilutions (50 uL) were performed in duplicate in a 96 microwell plate. Each well received 50 uL of iodinated OX40L-Fc (0.25 nM final concentration), was mixed and then the entire mixture was transferred to a 96 well tissue culture plate containing 30,000 OX40L-expressing CHO cells per well, which had been plated out the previous day. The plates were covered and incubated overnight at 4° C. The next day the wells (containing cells) were aspirated and washed twice with media buffer. 200 uL of 1N NaOH was added to each well to lyse the cells, shaken for 10 minute, and then transferred to a 96 well microtube. Each tube was counted in a Wallac gamma scintillation counter. The data was collected and plotted using Kaleidagraph. Curves were drawn using a 4-parameter fit.

The results of this experiment are shown in FIG. 3. Mabs 8E12 (open triangles) and 13G5 (solid squares) competed with OX40 receptor for binding to OX40L expressed on CHO cells, indicating that the antibodies inhibited the binding of human OX40 receptor to human OX40L.

Example 6

Treatment with Anti-OX40L Antibodies Inhibited T Cell Proliferation in a Cell-Based Assay Mixed Lymphocyte Reaction (MLR) assays were performed to determine whether blockade of OX40L-OX40 interaction by anti-OX40L mabs inhibited T cell proliferation. This cell-based experiment assays the ability of anti-OX40L antibodies to inhibit OX40L signaling. Briefly, plasmacytoid dendritic cells (pDCs) were isolated from human blood using BDCA-4 MACS beads according to the manufacturer's instructions (Miltenyi Biotec). Cells were set up at $1\times10^6$ cell/ml in media containing RPMI/10% fetal bovine serum/2 mM L-glutamine, and stimulated for 3 days with 2.5 ug/ml soluble human CD40L protein (R & D Systems) and 10 ng/ml human IL-3 protein (R & D Systems) in order to activate the pDCs. Activated (pDC) were then washed thrice with phosphate buffered saline/3% fetal bovine serum, then co-cultured with CD45RA+naïve T cells that were isolated from human blood using MACS beads according to manufacturer's instructions (Miltenyi Biotec). Co-culture was set up at a pDC:T cell ratio of 1:200, with $1\times10^5$ T cells per well of a U-bottom 96-well plate for 1 week in the presence of the indicated reagents. Cells were pulsed with 1 uCi methyl-tritiated thymidine per well during the last 6 hours of culture, harvested onto filter plates and counted.

Figure 4:
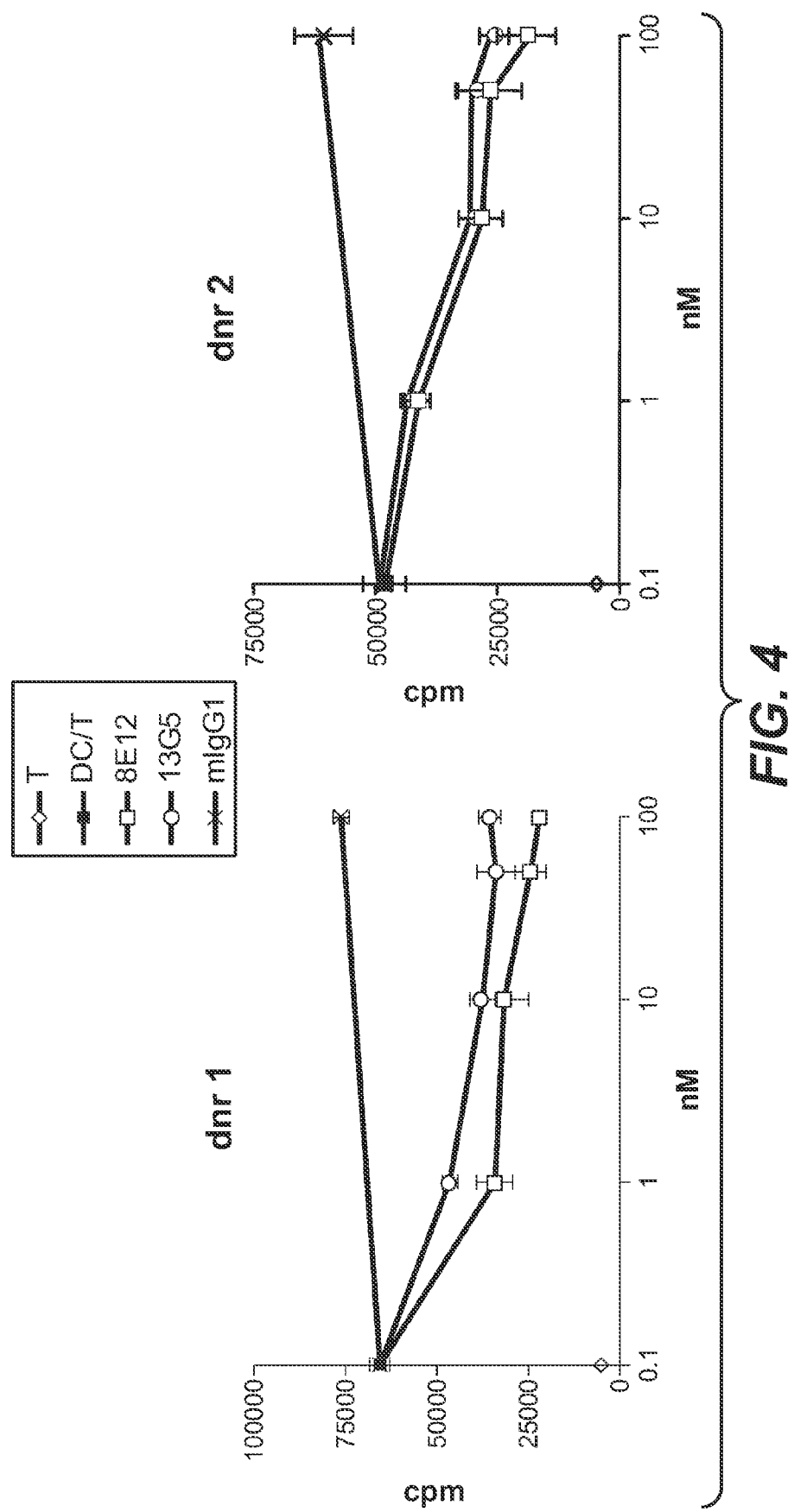
FIG. 4: graphically depicts that administration of anti-OX40L monoclonal antibodies 8E12 and 13G5 inhibited T-cell proliferation in a cell-based assay.

The results of two sets of experiments, termed "dnr1" and "dnr2", are shown in FIG. 4. Treatment with anti-OX40L mab 8E12 (open squares) and mab 13G5 (open circles) each significantly inhibited T-cell proliferation, indicating that both antibodies inhibit OX40L signaling. By contrast, control mouse IgG1 (X's) did not inhibit T-cell proliferation. Control levels of T cell proliferation is shown by open diamonds and that of T cells mixed with activated picky solid squares. The IC50 value for anti-OX40L mab inhibition of T cell proliferation varied from donor to donor, in a range of 0.5 to 10 nM.

Example 7

Treatment with Anti-OX40L Antibodies Inhibited IL-2 Production by T Memory Cells IL-2 production by T memory cells was assessed to determine whether blockade of OX40L-OX40 interaction by anti-OX40L mabs inhibited IL-2 production. This experiment tests the ability of anti-OX40L antibodies to inhibit OX40L signaling. Briefly, CD45RO+memory T cells were isolated from human blood using MACS beads according to manufacturer's instructions (Miltenyi Biotec). Cells were set up at $1\times10^6$ c/ml in media containing RPMI/10% fetal bovine serum/2 mM L-glutamine, and stimulated with 1 ug/ml anti-CD3 antibody (BD Pharmingen) and 10 nM soluble human OX40L protein (R & D Systems) for 16 hours. Anti-OX40L antibodies or control mIgG1 antibody were added at indicated concentrations. Levels of IL-2 in the supernatants were measured using an ELISA kit as per manufacturer's instructions (R & D Systems).

Figure 5:
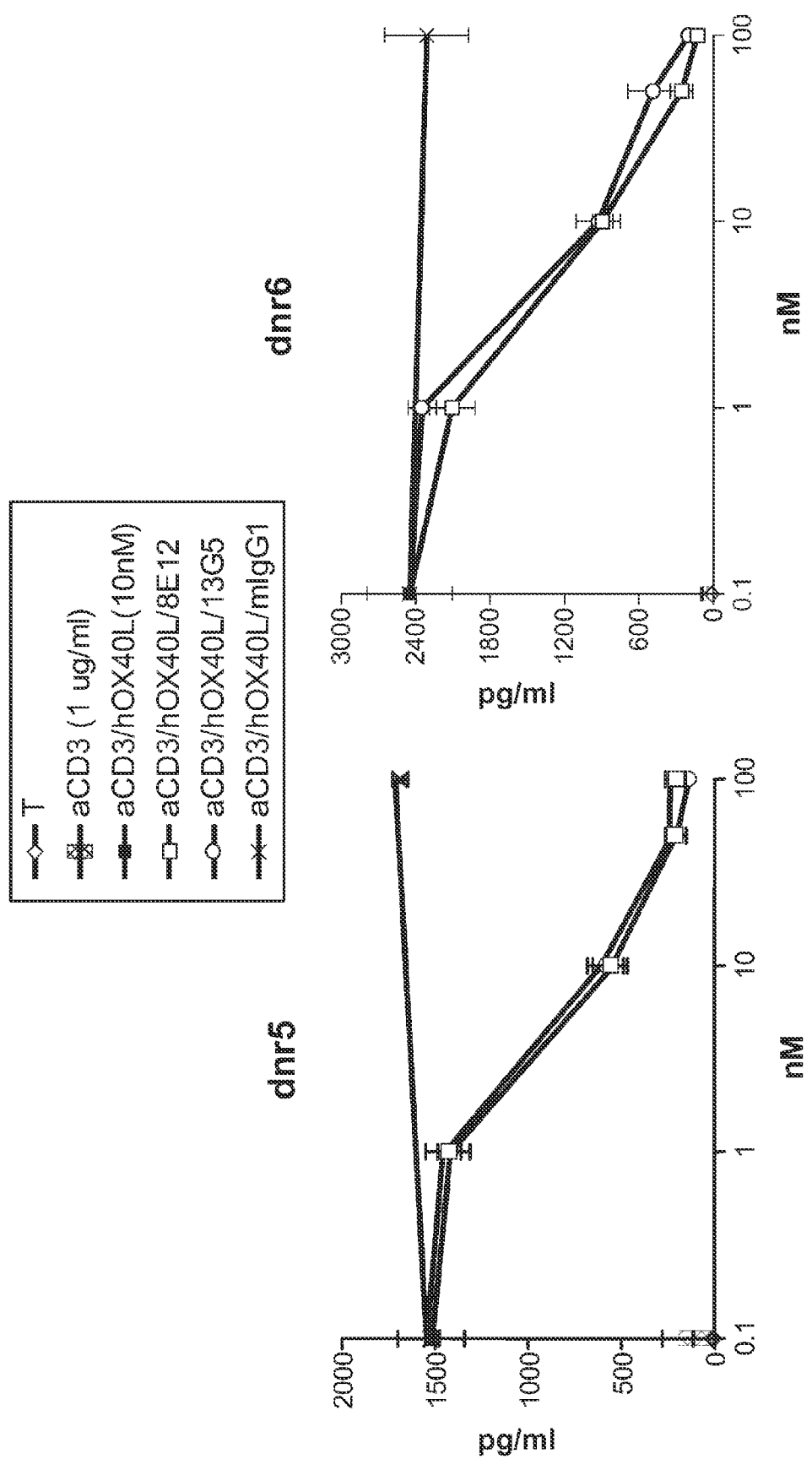
FIG. 5: graphically depicts that administration of anti-OX40L monoclonal antibodies 8E12 and 13G5 inhibited IL-2 production by T memory cells.

The results of two sets of experiments, termed "dnr5" and "dnr6" are shown in FIG. 5. Treatment with mab 8E12 (open squares) and mab 13G5 (open circles) each significantly inhibited IL-2 production by T memory cells. By contrast, addition of control mouse IgG1 (X's) did not inhibit IL-2 production. Levels of IL-2 production by memory T cells upon anti-CD3 antibody treatment alone is shown by hatched squares, upon anti-CD3 antibody and human OX40L treatment alone by solid squares, or T memory cells alone is shown by open diamonds.

Example 8

Treatment with Anti-OX40L Antibodies Inhibited Survival of Activated T Cells

Survival of activated T cells was assessed to determine whether blockade of OX40L-OX40 interaction by anti-OX40L mabs inhibited survival. This cell-based experiment assays the ability of anti-OX40L antibodies to inhibit OX40L signaling. Briefly, plasmacytoid dendritic cells (pDCs) were isolated from human blood using BDCA-4 MACS beads according to manufacturer's instructions (Miltenyi Biotec). Cells were set up at $1\times10^6$ cell/ml in media containing RPMI/

10% fetal bovine serum/2 mM L-glutamine and stimulated with 2.5 ug/ml soluble human CD40L protein (R & D Systems) and 10 ng/ml human IL-3 protein (R & D Systems) for 3 days. CD123+BDCA2-activated pDCs were then FACS sorted and co-cultured with activated T cells. T cells were isolated by negative selection from human blood using MACS beads according to manufacturer's instructions (Miltenyi Biotec) and activated for 3 days with 0.1 ug/ml anti-CD3/1 ug/ml anti-CD28 (BD Pharmingen). Co-culture was set up at a pDC:T cell ratio of 1:50, with $1 \times 10^6$ T cells per ml of a 6-well plate in the presence of the indicated reagents (at 1 nM or 10 nM concentrations). Cell numbers were assayed over time by trypan blue exclusion.

Figure 6:
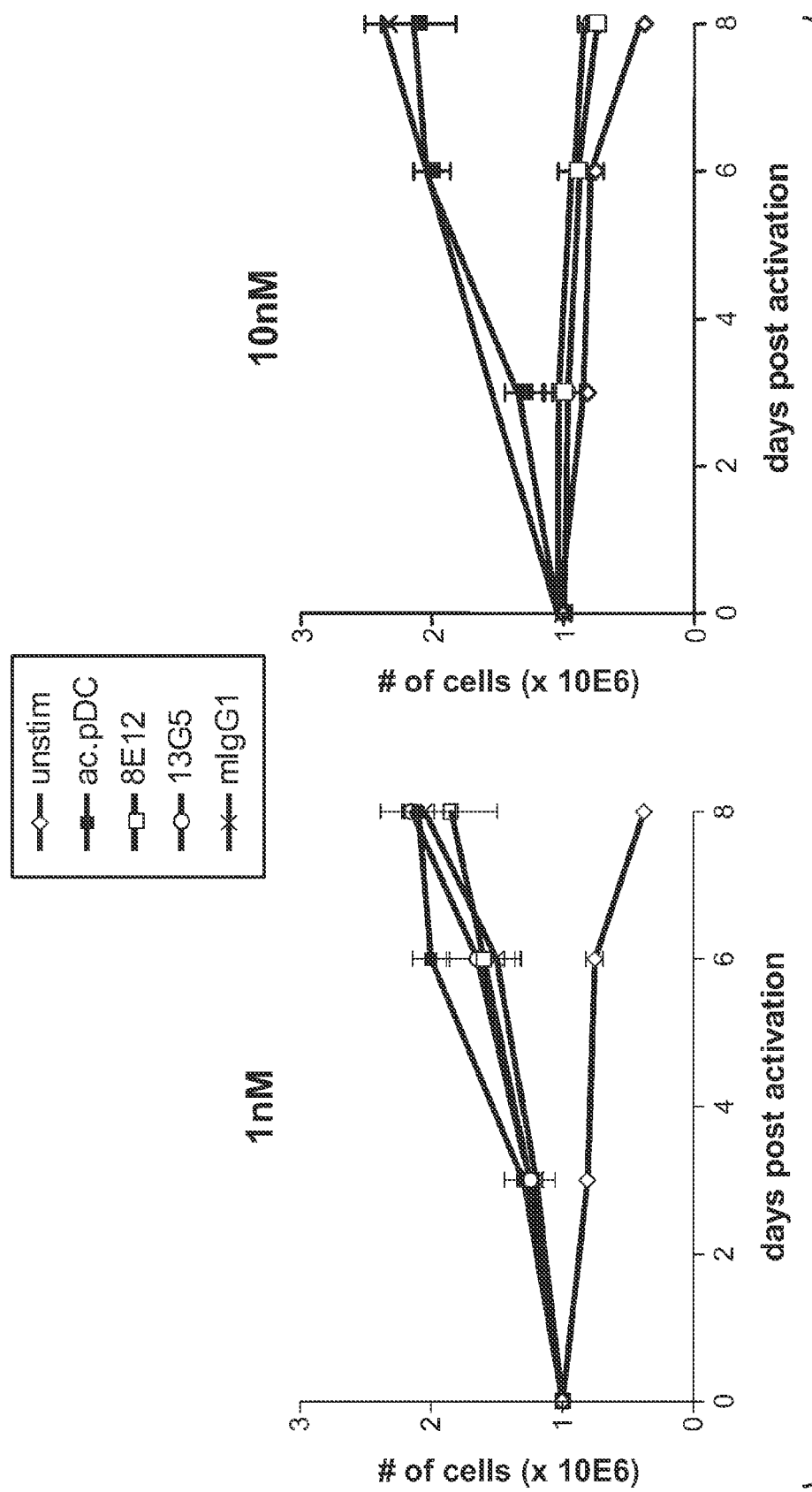
FIG. 6: graphically depicts that administration of anti-OX40L monoclonal antibodies 8E12 and 13G5 inhibited survival of activated T cells.

The results of the experiments are shown in FIG. 6. Treatment with anti-OX40L mab 8E12 (open squares) and mab 13G5 (open circles) each significantly inhibited survival of activated T cells. By contrast, addition of control mouse IgG1 ("mIgG1"; X's) did not inhibit survival of activated T cells. Control of T cells alone ("unstim") is shown by open diamonds, and control of T cells with activated pDCs ("ac. pDC") is shown by solid squares.

Although the foregoing invention has been described in some detail by way of illustration and example for purposes of clarity of understanding, the descriptions and examples should not be construed as limiting the scope of the invention.

What is claimed is:

1. An isolated anti-OX40L antibody comprising:
   (a) a light chain comprising (i) HVR-L1 comprising sequence RSSQSIVHGNGNTYLE (SEQ ID NO: 1) or RSSQSPVHSNGNTYLH (SEQ ID NO:2); (ii) HVR-L2 comprising sequence RVSNRFS (SEQ ID NO:3) or KVSNRFS (SEQ ID NO:4); and (iii) HVR-L3 comprising sequence FQGSHVPYT (SEQ ID NO:5) or SQSTHIPWT (SEQ ID NO:6); and
   (b) a heavy chain comprising (i) HVR-H1 comprising sequence SYWLN (SEQ ID NO:7) or SYWMH (SEQ ID NO:8); (ii) HVR-H2 comprising sequence MIDPSDSETHYNQVFKD (SEQ ID NO:9) or EIDPSNGRTNYNEKFKS (SEQ ID NO: 10); and (iii) HVR-H3 comprising sequence GRGNFYGGSHAMEY (SEQ ID NO: 11) or ERSPRYFDV (SEQ ID NO: 12),
   wherein the anti-OX40L antibody binds OX40L.

2. The anti-OX40L antibody of claim 1, wherein the antibody comprises:
   (a) a light chain comprising (i) HVR-L1 comprising sequence RSSQSIVHGNGNTYLE (SEQ ID NO: 1); (ii) HVR-L2 comprising sequence RVSNRFS (SEQ ID NO:3); and (iii) HVR-L3 comprising sequence FQGSHVPYT (SEQ ID NO:5); and
   (b) a heavy chain comprising (i) HVR-H1 comprising sequence SYWLN (SEQ ID NO:7); (ii) HVR-H2 comprising sequence MIDPSDSETHYNQVFKD (SEQ ID NO:9); and (iii) HVR-H3 comprising sequence GRGNFYGGSHAMEY (SEQ ID NO: 11).

3. The anti-OX40L antibody of claim 1, wherein the antibody comprises:
   (a) a light chain comprising (i) HVR-L1 comprising sequence RSSQSPVHSNGNTYLH (SEQ ID NO:2); (ii) HVR-L2 comprising sequence KVSNRFS (SEQ ID NO:4); and (iii) HVR-L3 comprising sequence SQSTHIPWT (SEQ ID NO:6); and
(b) a heavy chain comprising (i) HVR-H1 comprising sequence SYWMH (SEQ ID NO:8); (ii) HVR-H2 comprising sequence EIDPSNGRTNYNEKFKS (SEQ ID NO: 10); and (iii) HVR-H3 comprising sequence ERSPRYFDV (SEQ ID NO: 12).

4. The anti-OX40L antibody of claim 1, wherein the antibody comprises: a light chain variable domain having the sequence:

DILMTQTPLSLPVSLPVSLGDQASISCRSSQSIVHGNGNTYLEWHLQKPGQSPKLLIYRVSNRFSGVPDRFSGSGSG (SEQ ID NO: 13)
TDFTLKINRVEAEDLGVYYCFQGSHVPYTFGGGTKVEIKR.

5. The anti-OX40L antibody of claim 1, wherein the antibody comprises: a heavy chain variable domain having the sequence:

QVQLQQPGAELVRPGASVkLSCKASGYTFTSYWLNWVKQRPGQGLEWIVMIDPSDSETHYNQVFKDKATL (SEQ ID NO: 15)
TVDKSSSTAYMQLSSLTSEDSAVYYCIRGRGNFYGGSHAMEYWGQGTLLTVSS.

6. The anti-OX40L antibody of claim 1, wherein the antibody comprises:
(a) a light chain variable domain having the sequence:

DILMTQTPLSLPVSLGDQASISCRSSQSIVHGNGNTYLEWHLQKPGQSPKLLIYRVSNRFSGVPDRFSGSGSG (SEQ ID NO: 13)
TDFTLKINRVEAEDLGVYYCFQGSHVPYTFGGGTKVEIKR;
and (b) a heavy chain variable domain having the sequence:

(SEQ ID NO: 15)
QVQLQQPGAELVRPGASVKLSCKASGYTFTSYWLNWVKQRPGQGLEWIV
MIDPSDSETHYNQVFKDKATLTVDKSSSTAYMQLSSLTSEDSAVYYCIR
GRGNFYGGSHAMEYWGQGTLLTVSS.

7. The anti-OX40L antibody of claim 1, wherein the antibody comprising: a light chain variable domain having the sequence:

DIVMTQTPLSLPVSLGDQASMYCRSSQSPVHSNGNTYLHWYLQKPGQSPKLLIYKVSNRFSGVPDRFSGSGS (SEQ ID NO: 14)
GTDFTLKISRVEAEDLGVYFCSQSTHIPWTFGGGTKVEIKR.

8. The anti-OX40L antibody of claim 1, wherein the antibody comprises: a heavy chain variable domain having the sequence:

QVQLQQPGAELVKPGTSVKLSCKASGYSFTSYWMHGVRQRPGQGLEWIGEIDPSNGRTNYNEKFKSKATL (SEQ ID NO: 16)
TVDKSSSTAYIQLSSLTSEDSAVYYCTRERSPRYFDVWGAGTTLTVSS.

9. The anti-OX40L antibody of claim 1, wherein the antibody comprises:

(a) a light chain variable domain having the sequence:

```
DIVMTQTPLSLPVSLGDQASMYCRSSQSPVHSNGNTYLHWYLQKPGQSPKLLIYKVSNRFSGVPDRFSGSGS    (SEQ ID NO: 14)
GTDFTLKISRVEAEDLGVYFCSQSTHIPWTFGGGTKVEIKR;
and
```

(b) a heavy chain variable domain having the sequence:

```
QVQLQQPGAELVKPGTSVKLSCKASGYSFTSYWMHGVRQRPGQGLEWIGEIDPSNGRTNYNEKFKSKATL    (SEQ ID NO: 16)
TVDKSSSTAYIQLSSLTSEDSAVYYCTRERSPRYFDVWGAGTTLTVSS.
```

10. An isolated antibody that binds to a same epitope on human OX40L as the antibody of claim 6.

11. An isolated antibody that binds to a same epitope on human OX40L as the antibody of claim 9.

12. An isolated antibody that competes with an antibody of claim 6.

13. An isolated antibody that competes with an antibody of claim 9.

14. The antibody of claim 1, 2, 3, 6, 9, 10 or 11, wherein the antibody is a monoclonal antibody.

15. The antibody of claim 1, 2, 3, 6, 9, 10, or 11, wherein the antibody is selected from the group consisting of a chimeric antibody, a humanized antibody, an affinity matured antibody, and a bispecific antibody.

16. The antibody of claim 1, 2, 3, 6, 9, 10, or 11, wherein the antibody is an antibody fragment.

17. A nucleic acid encoding an antibody of any of claims 1, 2, 3, 6, 9, 10 or 11.

18. A vector comprising the nucleic acid of claim 17.

19. The vector of claim 18, wherein the vector is an expression vector.

20. An isolated host cell comprising a vector of claim 19.

21. The host cell of claim 20, wherein the host cell is prokaryotic.

22. The host cell of claim 20, wherein the host cell is eukaryotic.

23. The host cell of claim 20, wherein the host cell is mammalian.

24. A method for making an anti-OX40L antibody, said method comprising culturing a host cell comprising nucleic acid encoding the antibody of claim 1, 2, 3, 6, or 9 so that the nucleic acid is expressed.

25. The method of claim 24, wherein the host cell is prokaryotic.

26. The method of claim 24, wherein the host cell is eukaryotic.

27. A method for treating an immune disorder associated with expression or activity of OX40L, the method comprising administering an effective amount of the anti-OX40L antibody of any of claims 1, 2, 3, 6, 9, 10, or 11 to a subject in need of such treatment.

28. A composition comprising an anti-OX40L antibody of any of claim 1, 2, 3, or 9.

29. A composition comprising a nucleic acid of claim 17.

30. The composition of claim 28, wherein the composition further comprises a carrier.

31. The method of claim 24, further comprising recovering the antibody from the host cell culture.

32. The method of claim 31, where in the antibody is recovered from the host cell culture medium.

33. The method of claim 31, further comprising combining the recovered antibody with a pharmaceutically acceptable carrier, excipient, or carrier to prepare a pharmaceutical formulation comprising the antibody.

34. A method for making an anti-OX40L antibody, said method comprising culturing a host cell comprising nucleic acid encoding the antibody of claim 10 or 11 so that the nucleic acid is expressed.

35. The method of claim 34, further comprising recovering the antibody from the host cell culture.

36. The method of claim 35, where in the antibody is recovered from the host cell culture medium.

37. The method of claim 35, further comprising combining the recovered antibody with a pharmaceutically acceptable carrier, excipient, or carrier to prepare a pharmaceutical formulation comprising the antibody.

* * * * *

```
                        SEQUENCE LISTING

<160> NUMBER OF SEQ ID NOS: 16

<210> SEQ ID NO 1
<211> LENGTH: 16
<212> TYPE: PRT
<213> ORGANISM: Mus musculus

<400> SEQUENCE: 1

Arg Ser Ser Gln Ser Ile Val His Gly Asn Gly Asn Thr Tyr Leu
 1               5                  10                  15

Glu

<210> SEQ ID NO 2
<211> LENGTH: 16
<212> TYPE: PRT
<213> ORGANISM: Mus musculus

<400> SEQUENCE: 2

Arg Ser Ser Gln Ser Pro Val His Ser Asn Gly Asn Thr Tyr Leu
 1               5                  10                  15

His

<210> SEQ ID NO 3
<211> LENGTH: 7
<212> TYPE: PRT
<213> ORGANISM: Mus musculus

<400> SEQUENCE: 3

Arg Val Ser Asn Arg Phe Ser
                    5

<210> SEQ ID NO 4
<211> LENGTH: 7
<212> TYPE: PRT
<213> ORGANISM: Mus musculus

<400> SEQUENCE: 4

Lys Val Ser Asn Arg Phe Ser
                    5

<210> SEQ ID NO 5
<211> LENGTH: 9
<212> TYPE: PRT
<213> ORGANISM: Mus musculus

<400> SEQUENCE: 5

Phe Gln Gly Ser His Val Pro Tyr Thr
                    5
```

<210> SEQ ID NO 6
<211> LENGTH: 9
<212> TYPE: PRT
<213> ORGANISM: Mus musculus

<400> SEQUENCE: 6

Ser Gln Ser Thr His Ile Pro Trp Thr
                5

<210> SEQ ID NO 7
<211> LENGTH: 5
<212> TYPE: PRT
<213> ORGANISM: Mus musculus

<400> SEQUENCE: 7

Ser Tyr Trp Leu Asn
                5

<210> SEQ ID NO 8
<211> LENGTH: 5
<212> TYPE: PRT
<213> ORGANISM: Mus musculus

<400> SEQUENCE: 8

Ser Tyr Trp Met His
                5

<210> SEQ ID NO 9
<211> LENGTH: 17
<212> TYPE: PRT
<213> ORGANISM: Mus musculus

<400> SEQUENCE: 9

Met Ile Asp Pro Ser Asp Ser Glu Thr His Tyr Asn Gln Val Phe
 1               5                  10                  15

Lys Asp

<210> SEQ ID NO 10
<211> LENGTH: 17
<212> TYPE: PRT
<213> ORGANISM: Mus musculus

<400> SEQUENCE: 10

Glu Ile Asp Pro Ser Asn Gly Arg Thr Asn Tyr Asn Glu Lys Phe
 1               5                  10                  15

Lys Ser

<210> SEQ ID NO 11
<211> LENGTH: 14
<212> TYPE: PRT
<213> ORGANISM: Mus musculus

<400> SEQUENCE: 11

Gly Arg Gly Asn Phe Tyr Gly Gly Ser His Ala Met Glu Tyr
                5                  10

<210> SEQ ID NO 12
<211> LENGTH: 9
<212> TYPE: PRT
<213> ORGANISM: Mus musculus

<400> SEQUENCE: 12

-continued

Glu Arg Ser Pro Arg Tyr Phe Asp Val
                5

<210> SEQ ID NO 13
<211> LENGTH: 113
<212> TYPE: PRT
<213> ORGANISM: Mus musculus

<400> SEQUENCE: 13

Asp Ile Leu Met Thr Gln Thr Pro Leu Ser Leu Pro Val Ser Leu
 1               5                  10                  15

Gly Asp Gln Ala Ser Ile Ser Cys Arg Ser Ser Gln Ser Ile Val
                20                  25                  30

His Gly Asn Gly Asn Thr Tyr Leu Glu Trp His Leu Gln Lys Pro
                35                  40                  45

Gly Gln Ser Pro Lys Leu Leu Ile Tyr Arg Val Ser Asn Arg Phe
                50                  55                  60

Ser Gly Val Pro Asp Arg Phe Ser Gly Ser Gly Ser Gly Thr Asp
                65                  70                  75

Phe Thr Leu Lys Ile Asn Arg Val Glu Ala Glu Asp Leu Gly Val
                80                  85                  90

Tyr Tyr Cys Phe Gln Gly Ser His Val Pro Tyr Thr Phe Gly Gly
                95                 100                 105

Gly Thr Lys Val Glu Ile Lys Arg
               110

<210> SEQ ID NO 14
<211> LENGTH: 113
<212> TYPE: PRT
<213> ORGANISM: Mus musculus

<400> SEQUENCE: 14

Asp Ile Val Met Thr Gln Thr Pro Leu Ser Leu Pro Val Ser Leu
 1               5                  10                  15

Gly Asp Gln Ala Ser Met Tyr Cys Arg Ser Ser Gln Ser Pro Val
                20                  25                  30

His Ser Asn Gly Asn Thr Tyr Leu His Trp Tyr Leu Gln Lys Pro
                35                  40                  45

Gly Gln Ser Pro Lys Leu Leu Ile Tyr Lys Val Ser Asn Arg Phe
                50                  55                  60

Ser Gly Val Pro Asp Arg Phe Ser Gly Ser Gly Ser Gly Thr Asp
                65                  70                  75

Phe Thr Leu Lys Ile Ser Arg Val Glu Ala Glu Asp Leu Gly Val
                80                  85                  90

Tyr Phe Cys Ser Gln Ser Thr His Ile Pro Trp Thr Phe Gly Gly
                95                 100                 105

Gly Thr Lys Val Glu Ile Lys Arg
               110

<210> SEQ ID NO 15
<211> LENGTH: 123
<212> TYPE: PRT
<213> ORGANISM: Mus musculus

<400> SEQUENCE: 15

Gln Val Gln Leu Gln Gln Pro Gly Ala Glu Leu Val Arg Pro Gly
 1               5                  10                  15

Ala Ser Val Lys Leu Ser Cys Lys Ala Ser Gly Tyr Thr Phe Thr

```
                          20                  25                  30
Ser Tyr Trp Leu Asn Trp Val Lys Gln Arg Pro Gly Gln Gly Leu
                  35                  40                  45

Glu Trp Ile Val Met Ile Asp Pro Ser Asp Ser Glu Thr His Tyr
                  50                  55                  60

Asn Gln Val Phe Lys Asp Lys Ala Thr Leu Thr Val Asp Lys Ser
                  65                  70                  75

Ser Ser Thr Ala Tyr Met Gln Leu Ser Ser Leu Thr Ser Glu Asp
                  80                  85                  90

Ser Ala Val Tyr Tyr Cys Ile Arg Gly Arg Gly Asn Phe Tyr Gly
                  95                 100                 105

Gly Ser His Ala Met Glu Tyr Trp Gly Gln Gly Thr Leu Leu Thr
                 110                 115                 120

Val Ser Ser

<210> SEQ ID NO 16
<211> LENGTH: 118
<212> TYPE: PRT
<213> ORGANISM: Mus musculus

<400> SEQUENCE: 16

Gln Val Gln Leu Gln Gln Pro Gly Ala Glu Leu Val Lys Pro Gly
 1               5                  10                  15

Thr Ser Val Lys Leu Ser Cys Lys Ala Ser Gly Tyr Ser Phe Thr
                  20                  25                  30

Ser Tyr Trp Met His Gly Val Arg Gln Arg Pro Gly Gln Gly Leu
                  35                  40                  45

Glu Trp Ile Gly Glu Ile Asp Pro Ser Asn Gly Arg Thr Asn Tyr
                  50                  55                  60

Asn Glu Lys Phe Lys Ser Lys Ala Thr Leu Thr Val Asp Lys Ser
                  65                  70                  75

Ser Ser Thr Ala Tyr Ile Gln Leu Ser Ser Leu Thr Ser Glu Asp
                  80                  85                  90

Ser Ala Val Tyr Tyr Cys Thr Arg Glu Arg Ser Pro Arg Tyr Phe
                  95                 100                 105

Asp Val Trp Gly Ala Gly Thr Thr Leu Thr Val Ser Ser
                 110                 115
```